US005656653A

United States Patent [19]

Booher et al.

[11] Patent Number: 5,656,653
[45] Date of Patent: Aug. 12, 1997

[54] 6-HETEROCYCLIC-4-AMINO-1,2,2A,3,4,5-HEXAHYDROBENZ[CD]INDOLES

[75] Inventors: Richard N. Booher, Indianapolis; David E. Lawhorn, Greenfield; Michael J. Martinelli; Charles J. Paget, Jr., both of Indianapolis; John M. Schaus, Zionsville, all of Ind.

[73] Assignee: Eli Lilly and Company, Indianapolis, Ind.

[21] Appl. No.: 459,564

[22] Filed: Jun. 2, 1995

Related U.S. Application Data

[62] Division of Ser. No. 263,910, Jun. 20, 1994, which is a division of Ser. No. 954,171, Sep. 30, 1992, Pat. No. 5,347,013, which is a continuation-in-part of Ser. No. 676,679, Mar. 28, 1991, Pat. No. 5,244,911.

[51] Int. Cl.$^6$ .................................................. A61K 31/40
[52] U.S. Cl. ............................. 514/406; 548/364.7
[58] Field of Search ........................ 514/406; 548/364.7

[56] References Cited

U.S. PATENT DOCUMENTS

| | | | |
|---|---|---|---|
| 2,809,974 | 10/1957 | Kornfeld et al. | 548/430 |
| 3,336,307 | 8/1967 | Shen . | |
| 3,671,541 | 6/1972 | Bormann et al. | 548/436 |
| 3,674,801 | 7/1972 | Bormann et al. | 548/436 |
| 4,057,560 | 11/1977 | Bormann et al. | 548/436 |
| 4,110,339 | 8/1978 | Bach et al. | 514/411 |
| 4,576,959 | 3/1986 | Flaugh | 514/411 |
| 4,745,126 | 5/1988 | Leander | 514/411 |
| 4,977,172 | 12/1990 | Johnson et al. | 514/374 |
| 4,983,622 | 1/1991 | Flaugh | 514/411 |
| 5,021,438 | 6/1991 | Junge et al. | 548/221 |
| 5,039,820 | 8/1991 | Kress et al. | 548/436 |
| 5,204,340 | 4/1993 | Flaugh et al. | 514/210 |
| 5,212,319 | 5/1993 | Kress et al. | 548/436 |
| 5,229,410 | 7/1993 | Flaugh et al. | 514/411 |
| 5,302,612 | 4/1994 | Flaugh et al. | 514/411 |
| 5,397,799 | 3/1995 | Kress et al. | 514/411 |

FOREIGN PATENT DOCUMENTS

| | | |
|---|---|---|
| 566758 | 7/1985 | Australia . |
| 2064363 | 9/1992 | Canada . |
| 091328 | 10/1983 | European Pat. Off. . |
| 148440 | 7/1985 | European Pat. Off. . |
| 153083 | 8/1985 | European Pat. Off. . |
| 162695 | 11/1985 | European Pat. Off. . |
| 332968 | 9/1989 | European Pat. Off. . |
| 399982 | 11/1990 | European Pat. Off. . |
| 506369 | 9/1992 | European Pat. Off. . |
| 3525564 | 2/1987 | Germany . |
| 517732 | 2/1972 | Switzerland . |
| 90/04396 | 5/1990 | WIPO . |

OTHER PUBLICATIONS

Dorland's Illustrated Medical Dictionary 26th ed., Saunders, Philadelphia, 1981 p. 1193.
Burger, ed. Medicinal Chemistry, 2d Ed. Interscience, NY p. 42 (1960).
Flaugh, et al., *J. Med. Chem.*, 31, 1746–1753 (1988).
Kornfeld, et al., *J.A.C.S.*, 78, 3087 (1956).
Kruse, et al., *J. Org. Chem.*, 49, 4761–4768 (1984).
Bach, et al., *J. Med. Chem.*, 23, 481–491 (1980).
Glennon, *J. Med. Chem.*, 30,1 (1987).
T.W. Greene, *Protective Group in Organic Synthesis*, John Wiley and Sons (1981) Chapter 7, pp. 218–287.
J.W. Barton, *Protective Group in Organic Synthesis*, McOmie, ed., Plenum Press (1973) Chapter 2, pp. 43–61.
Schoenberg, et al., *J. Org. Chem.*, 39, 3327 (1974).
Schoenberg, et al., *J. Org. Chem.*, 39, 3318 (1974).
*Tetrahedron Letters*, 21, 4061 (1980).
Nichols, et al., *Org. Prep. & Proc. Int.*, 9, 277 (1977).
Leanna, et a l., *Tet. Lett.*, 30, 3935 (1989).
O. Mitsunobu, *Synthesis*, Jan. 1981, p. 1.
J. P. Freemen, et al., *Synthesis*, Dec. 1974, p. 894.
Sugi, et al., *Bull Chem. Soc. Jap.*, 43, 1489 (1970).
Morrison & Boyd, Chapter 22, *Organic Chemistry*, 3rd Ed. (1973).
Wong, et al., *J. Neural Transm.*, 71, 207–218 (1988).
Wong, et al., *J. Neural Transm.*, 64, 251–269 (1985).

*Primary Examiner*—Donald G. Daus
*Attorney, Agent, or Firm*—Arleen Palmberg; Douglas J. Taylor; David E. Boone

[57] ABSTRACT

6-Heterocyclic-4-amino-1,2,2a,3,4,5-hexahydrobenz[cd] indoles are provided which are useful in modifying the function of serotonin in mammals.

11 Claims, No Drawings

6-HETEROCYCLIC-4-AMINO-1,2,2A,3,4,5-HEXAHYDROBENZ[CD]INDOLES

This application is a divisional application of application Ser. No. 08263,910, filed Jun. 20, 1994, which is a divisional application of application Ser. No. 07/954,171, filed Sep. 30, 1992, now issued as U.S. Pat. No. 5,347,013, which is a continuation-in-part application of application Ser. No. 07/676,679, filed Mar. 28, 1991, now issued as U.S. Pat. No. 5,244,911.

FIELD OF THE INVENTION

This invention relates to 6-heterocyclic-4-amino-1,2,2a,3,4,5-hexahydrobenz[cd]indoles and their use in modifying the function of serotonin in a mammal.

BACKGROUND OF THE INVENTION

Flaugh in U.S. Pat. No. 4,576,959 (issued 1986) disclosed a family of 6-substituted-4-dialkylamino-1,3,4,5-tetrahydrobenz[cd]indoles which are described as central serotonin agonists. Leander in U.S. Pat. No. 4,745,126 (1988) disclosed a method for treating anxiety in humans employing a 4-substituted-1,3,4,5-tetrahydrobenz[cd]indole-6-carboxamide derivative.

European Patent Application 399,982 discloses certain heterocyclic-substituted aminotetralins. These compounds are disclosed as being serotonin agonists, partial agonists or antagonists.

It has now been found that certain 6-heterocyclic-substituted hexahydrobenz[cd]indoles are useful in treating conditions requiring modification of the serotonin function in the body.

SUMMARY OF THE INVENTION

This invention relates to compounds of the Formula 1

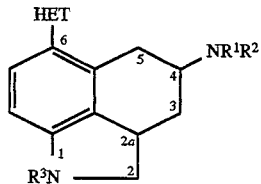

wherein:

$R^1$ is hydrogen, $C_1$–$C_4$ alkyl, $C_4$–$C_4$ alkenyl, cyclopropylmethyl, aryl($C_1$–$C_4$ alkyl), —$(CH_2)_nS(C_1$–$C_4$ alkyl), —$C(O)R^4$, —$(CH_2)_nC(O)NR^5R^6$;

$R^2$ is hydrogen, $C_1$–$C_4$ alkyl, cyclopropylmethyl or $C_3$–$C_4$ alkenyl;

$R^3$ is hydrogen, $C_1$–$C_4$ alkyl or an amino-blocking group; n is 1–4;

$R^4$ is hydrogen, $C_1$–$C_4$ alkyl, $C_1$–$C_4$ haloalkyl, $C_1$–$C_4$ alkoxy or phenyl;

$R^5$ and $R^6$ are independently hydrogen, a $C_1$–$C_4$ alkyl, or a $C_5$–$C_8$ cycloalkyl, with the proviso that when one of $R^5$ or $R^6$ is a cycloalkyl the other is hydrogen;

HET is a tetrazolyl ring, a substituted tetrazolyl ring or an aromatic 5- or 6-membered heterocyclic ring, said ring having from one to three heteroatoms which are the same or different and which are selected from the group consisting of sulfur, oxygen, and nitrogen with the proviso that the 6-membered heterocyclic ring can only contain carbon and nitrogen and with the further proviso that the 5-membered ring may contain no more than one oxygen or one sulfur but not both oxygen and sulfur.

The invention also provides a pharmaceutical formulation comprising a compound of Formula 1 in combination with a pharmaceutically acceptable excipient therefor.

A further embodiment of the invention is a method for effecting a biological response at the $5HT_{1A}$ or $5HT_{1D}$ receptor by administering a compound of Formula 1. Another embodiment involves a method for treating a variety of conditions in a mammal which require regulation of serotonin functions by administering a compound of Formula 1.

DETAILED DESCRIPTION OF THE INVENTION

As used herein, the term "alkyl" represents a straight or branched alkyl chain having the indicated number of carbon atoms. For example, "$C_1$–$C_4$ alkyl" groups are methyl, ethyl, n-propyl, isopropyl, n-butyl, sec.-butyl, isobutyl and tert-butyl. "$C_1$–$C_8$ alkyl" groups include those listed for $C_1$–$C_4$ alkyl as well as n-pentyl, 2-methylbutyl, 3-methylbutyl, n-hexyl, 4-methylpentyl, n-heptyl, 3-ethylpentyl, 2-methylhexyl, 2,3-dimethylpentyl, n-octyl, 3-propylpentyl, 6-methylheptyl, and the like.

The term "$C_4$–$C_4$ alkenyl" refers to olefinically unsaturated alkyl groups such as —$CH_2CH=CH_2$, —$CH_2CH_2CH=CH_2$, —$CH(CH_3)CH=CH_2$ and the like.

The term "aryl" means an aromatic carbocyclic structure having six to ten carbon atoms. Examples of such ring structures are phenyl, naphthyl, and the like.

The term "cycloalkyl" means an aliphatic carbocyclic structure having the indicated number of carbon atoms in the ring. For example, the term "$C_3$–$C_7$ cycloalkyl" means cyclopropyl, cyclobutyl, cyclopentyl, cyclohexyl, and cycloheptyl.

The term "aryl ($C_1$–$C_4$ alkyl)" means an aryl structure joined to a $C_1$–$C_4$ alkyl group. Examples of such groups are benzyl, phenylethyl, α-methylbenzyl, 3-phenylpropyl, α-naphthylmethyl, β-naphthylmethyl, 4-phenylbutyl, and the like. Similarly the term "aryl ($C_1$–$C_3$ alkyl)" means an aromatic carbocyclic structure joined to a $C_1$–$C_3$ alkyl.

The $C_1$–$C_8$ alkyl, aryl, aryl ($C_1$–$C_4$ alkyl) and aryl ($C_1$–$C_3$ alkyl) groups can be substituted by one or two moieties. Typical aryl and/or alkyl substitutents are $C_1$–$C_3$ alkoxy, halo, hydroxy, $C_1$–$C_3$ thioalkyl, nitro, and the like. Moreover, the aryl, aryl ($C_1$–$C_4$ alkyl) and aryl ($C_1$–$C_3$ alkyl) groups can also be substituted by a $C_1$–$C_3$ alkyl or a trifluoromethyl group.

In the foregoing, the term "$C_1$–$C_3$ alkyl" means any of methyl, ethyl, n-propyl, and isopropyl; the term "$C_1$–$C_3$ alkoxy" means any of methoxy, ethoxy, n-propoxy, and isopropoxy; the term "halo" means any of fluoro, chloro, bromo, and iodo; and the term "$C_1$–$C_3$ thioalkyl" means any of methylthio, ethylthio, n-propylthio, and isopropylthio.

Examples of substituted $C_1$–$C_8$ alkyl are methoxymethyl, trifluoromethyl, 6-chlorohexyl, 2-bromopropyl, 2-ethoxy-4-iodobutyl, 3-hydroxypentyl, methylthiomethyl, and the like.

Examples of substituted aryl are p-bromophenyl, m-iodophenyl, p-tolyl, o-hydroxyphenyl, β-(4-hydroxy)-naphthyl, p-(methylthio)phenyl, m-trifluoromethylphenyl, 2-chloro-4-methoxyphenyl, α-(5-chloro)naphthyl, and the like.

Examples of substituted aryl ($C_1$–$C_4$ alkyl) are p-chlorobenzyl, o-methoxybenzyl, m-(methylthio)-α-methylbenzyl, 3-(4'-trifluoromethylphenyl)propyl, o-iodobenzyl, p-methylbenzyl, and the like.

The term "amino-blocking group" is used herein as it is frequently used in synthetic organic chemistry, to refer to a group which will prevent an amino group from participating in a reaction carried out on some other functional group of the molecule, but which can be removed from the amine when it is desired to do so. Such groups are discussed by T. W. Greene in chapter 7 of *Protective Groups in Organic Synthesis* John Wiley and Sons, New York, 1981, and by J. W. Barton in chapter 2 of *Protective Groups in Organic Chemistry* J. F. W. McOmie, ed., Plenum Press, New York, 1973, which are incorporated herein by reference in their entirety. Examples of such groups include benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. Preferred amino-blocking groups are benzyl (—$CH_2C_6H_5$), acyl [C(O)R] or $SiR_3$ where R is $C_1$–$C_4$ alkyl, halomethyl, or 2-halo-substituted-($C_2$–$C_4$ alkoxy).

The term "aromatic 5- or 6-membered heterocyclic ring" refers to a ring containing from one to three heteroatoms which can be nitrogen, oxygen or sulfur. The 5-membered heterocyclic rings can contain carbon and nitrogen atoms and up to one oxygen or one sulfur but not one of each. In 5-membered rings not containing oxygen or sulfur, one nitrogen can be substituted with either a hydrogen, $C_1$–$C_3$ alkyl, phenyl or ($C_1$–$C_3$ alkyl)phenyl group. The 6-membered heterocyclic rings can contain carbon and nitrogen atoms only. The 5- or 6-membered rings can have one or two of the carbon atoms in the ring substituted independently with $C_1$–$C_3$ alkyl, halogen, OH, $C_1$–$C_3$ alkoxy, $C_1$–$C_3$ alkylthio, $NH_2$, CN or phenyl. Adjacent carbons in the heterocyclic ring may be connected with a —CH=CH—CH=CH— bridge to form a benzo-fused ring on the heterocycle.

These aromatic 5- or 6-membered heterocyclic rings can be either substituted or unsubstituted and include furan, thiophene, thiazole, oxazole, isoxazole, isothiazole, oxadiazole, thiadiazole, pyridine, pyridazine, pyrimidine, pyrazine, pyrrole, pyrazole, imidazole, and triazole. The heterocyclic ring can be attached to the benzene ring by any carbon in the heterocyclic ring, for example, 2- or 3-furan.

The term "substituted tetrazolyl ring" refers to a tetrazolyl ring system which has a $C_1$–$C_3$ alkyl or phenyl substituent on the 2-position nitrogen atom of such ring system.

As used herein the following terms refer to the structure indicated and include all of the structural isomers:

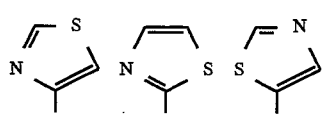

Thiazoles

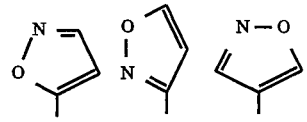

Isoxazoles

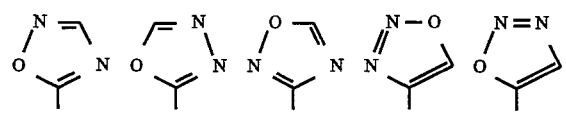

Oxadiazoles

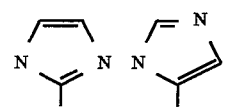

Imidazoles

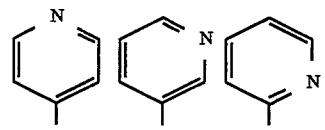

Pyridines

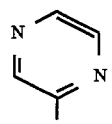

Pyrazine

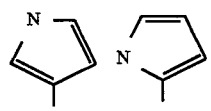

Pyrroles

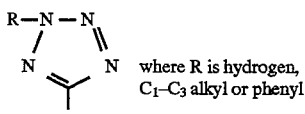 where R is hydrogen, $C_1$–$C_3$ alkyl or phenyl

Tetrazole

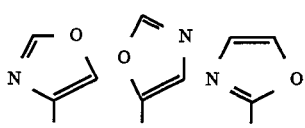

Oxazoles

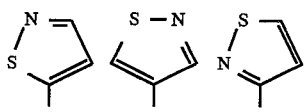

Isothiazoles

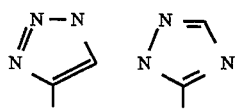

Triazoles

-continued

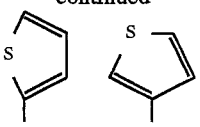

Thiophenes

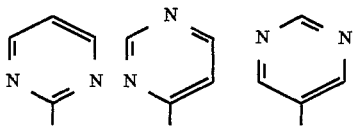

Pyrimidines

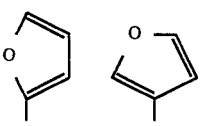

Furans

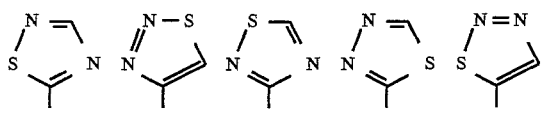

Thiadiazoles

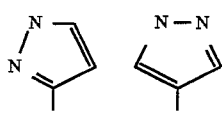

Pyrazoles

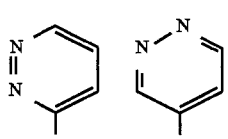

Pyridazines

While all of the compounds of the invention are useful for the purposes taught herein, certain of the present compounds are preferred for such uses. Preferably $R^1$ and $R^2$ are both $C_1$–$C_4$ alkyl, particularly n-propyl, $R^3$ is hydrogen, and HET is one of the following isoxazole, oxazole, pyrazole, pyridine, thiazole, furan, thiophene or oxadiazole. Other preferred aspects of the present invention are noted hereinafter.

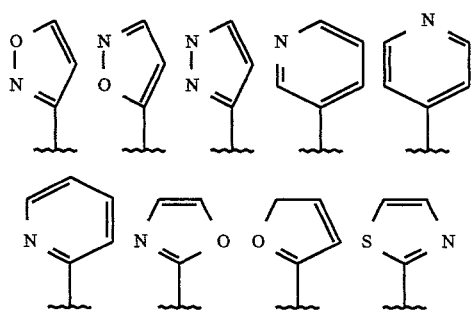

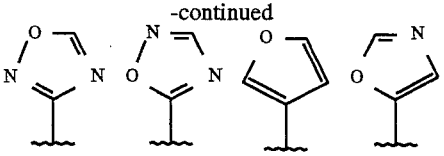

The compounds of the instant invention have at least two chiral centers and therefore at least four stereoisomers can exist for each. Chiral centers exist at positions 2a and 4 of Formula 1. If a substitutent group contains a chiral center, then additional stereoisomers can exist. Racemic mixtures as well as the substantially pure stereoisomers of Formula 1 are contemplated as within the scope of the present invention. By the term "substantially pure", it is meant that at least about 90 mole percent, more preferably at least about 95 mole percent and most preferably at least 98 mole percent of the desired stereoisomer is present compared to other possible stereoisomers. Particularly preferred stereoisomers of Formula 1 are those in which the configuration of the chiral center at position 2a is S and at position 4 is R, i.e., 2aS, 4R, or the configuration of the chiral center at position 2a is R and at position 4 is S, i.e., 2aR,4S.

The terms "R" and "S" are used herein as commonly used in organic chemistry to denote specific configuration of a chiral center. The term "R" refers to "right" and refers that configuration of a chiral center with a clockwise relationship of group priorities (highest to second lowest) when viewed along the bond toward the lowest priority group. The term "S" or "left" refers to that configuration of a chiral center with a counterclockwise relationship of group priorities (highest to second lowest) when viewed along the bond toward the lowest priority group. The priority of groups is based upon their atomic number (heaviest isotope first). A partial list of priorities and a discussion of stereochemistry is contained in the book: *The Vocabulary of Organic Chemistry* Orchin, et al., John Wiley and Sons Inc., publishers, page 126, which is incorporated herein by reference.

As set forth above, this invention includes the pharmaceutically acceptable salts of the compounds of Formula 1. Since the compounds of this invention are amines, they are basic in nature and accordingly react with any number of inorganic and organic acids to form pharmaceutically acceptable salts using acids such as hydrochloric acid, nitric acid, phosphoric acid, sulfuric acid, hydrobromic acid, hydroiodic acid, phosphorous acid and others, as well as salts derived from nontoxic organic acids such as aliphatic mono and dicarboxylic acids, amino acids, phenyl-substituted alkanoic acids, hydroxyalkanoic and hydroxyalkandioic acids, aromatic acids, aliphatic and aromatic sulfonic acids. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, tartrate, isobutyrate, caprate, heptanoate, propiolate, oxalate, malonate, succinate, suberate, sebacate, fumarate, maleate, mandelate, butyne-1,4-dioate, hexyne-1, 6-dioate, hippurate, benzoate, chlorobenzoate, methylbenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, naphthalene-1-sulfonate, naphthalene-2-sulfonate and mesylate.

Particularly preferred compounds of Formula 1 include the compounds in which $R^3$ is hydrogen, $R^1$ and $R^2$ are both either n-propyl or methyl and HET is 3-isoxazolyl, 5-isoxazolyl, 2-oxazolyl, 5-oxazolyl, 3-isothiazolyl, 5-isothiazolyl, 2-imidazolyl or 4-imidazolyl. These compounds include the racemic mixtures of possible stereoisomers as well as the substantially pure stereoisomers with different configurations at positions 2a and 4, i.e., 2aR, 4R or 2aR, 4S or 2aS, 4R or 2aS, 4S.

As depicted in Scheme I, the compounds of the present invention can be prepared by reacting a 4-amino-6-metallo-substituted hexahydrobenz[cd]indole as represented by structure 2 with a heterocyclic compound represented by structure 4. In structure 2, M represents a metallo moiety such as lithium, magnesium, zinc, tin, mercury, boronic acid (—$BO_2H_2$) and the like while Z is an amino-blocking group. When the metallo moiety is multivalent, it is normally associated with other moieties such as, for example, halo for magnesium (Grignard reagent) and alkyl groups for tin (trialkyltin). The heterocycle represented by structure 4 contains a leaving group "L", such as a chloro, bromo, or trifluoromethylsulfonoxy group, which can be displaced by the metallo-indole. The heterocycle can be substituted as set forth hereinabove.

Scheme 1

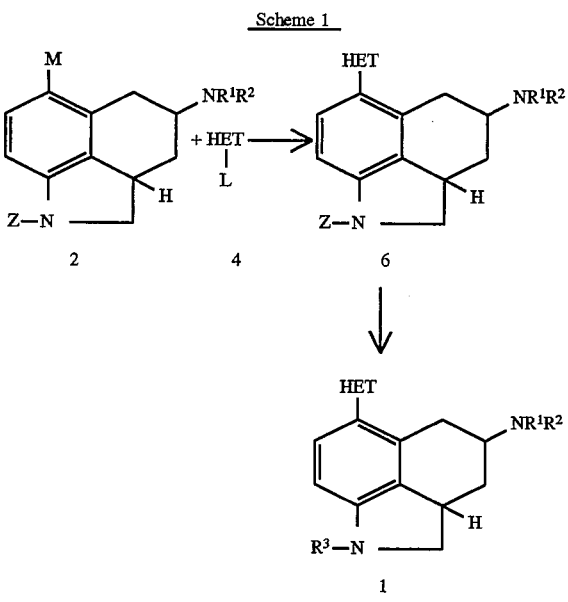

The reaction of the metallo-indoline 2 and heterocycle 4 is accomplished in the presence of a palladium or nickel catalyst such as Pd[P($C_6H_5$)$_3$]$_4$, PdCl$_2$, Pd[P($C_6H_5$)$_3$]$_2$Cl$_2$, Ni(acac)$_2$, NiCl$_2$[P($C_6H_5$)$_3$]$_2$ and the like, wherein "acac" represents acetylacetonate and "$C_6H_5$" represents a phenyl group. The organometallic reagent 2 is prepared by methods commonly used in the art for such preparations, for example, the lithium or magnesium reagents can be prepared by contacting the appropriate 6-chloro-, 6-bromo- or 6-iodo-substituted hexahydrobenzindole with an organolithium reagent or magnesium metal in a solvent such as ether or tetrahydrofuran. Other organometallic derivatives can be used such as zinc, tin, mercury or boronic acid (—$BO_2H_2$). The zinc, tin and mercury reagents can be prepared by reaction of the lithiated benzindole with a zinc, tin or mercury derivative such as zinc chloride, chlorotrialkylstannane, or mercuric chloride. The boronic acid derivative can be prepared by reacting the lithium reagent with trimethylborate followed by hydrolysis of the resulting boronate ester. Mercuric acetate can be contacted directly with the hexahydrobenzindole to provide the mercurated derivative.

The 1-nitrogen of the hexahydro benzindole is preferably protected with a group such as triphenylmethyl (trityl), benzyl, or benzoyl. These protecting groups are represented by Z in structures 2. The protecting group can be removed after the coupling reaction is accomplished to provide the 1-hydrobenzindole compound.

An alternative method of preparing the compounds of the instant invention involves contacting an organometallic reagent prepared from a heterocyclic compound with a 6-bromo or 6-iodo-4-aminobenzindole. The reaction is accomplished in the presence of a catalyst such as that used in reaction Scheme I. The metal in the organometallic derivative of the heterocycle can be lithium, magnesium (Grignard reagent), zinc, tin, mercury, or a boronic acid (—$BO_2H_2$). These organometallic compounds can be prepared by standard methods, as described above for the benzindoles. Alternatively, the lithiated heterocycles can be prepared by treating a heterocycle with a strong base such as an alkyllithium or a lithium dialkylamide.

Unless otherwise indicated, in the following preparation procedures, $R_a$ and $R_a'$ may independently be hydrogen, $C_1$–$C_3$ alkyl, halogen, OH, O($C_1$–$C_3$ alkyl), S($C_1$–$C_3$ alkyl), $NH_2$, CN, or phenyl. $R_b$ may be hydrogen, $C_1$–$C_3$ alkyl, phenyl, or ($C_1$–$C_3$ alkyl)phenyl. $R_c$ may be hydrogen or $C_1$–$C_3$ alkyl. $R_d$ may be OH, O($C_1$–$C_3$ alkyl), O(phenyl), O($C_1$–$C_3$ alkylphenyl), halo, S($C_1$–$C_3$ alkyl), S(phenyl), S($C_1$–$C_3$ alkylphenyl), $NH_2$, NH($C_1$–$C_3$ alkyl), N($C_1$–$C_3$ alkyl)$_2$, OCO($C_1$–$C_3$ alkyl), OCO(phenyl), OCO($C_1$–$C_3$ alkylphenyl) or the like.

In an alternative preparation procedure, compounds of the instant invention having a 5-membered heterocyclic ring in the 6-position can be prepared by the cycloaddition of a compound of the type represented in structure 8 wherein $R^1$ and $R^2$ are as defined above and B is an amino-protecting group or hydrogen,

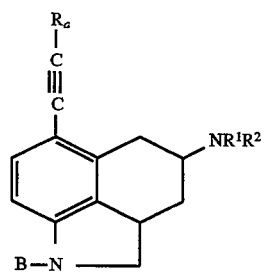

with a 1,3-dipole of the type $^{+T}$=U–V$^-$ in which T, U, and V can be selected from the following list of (a) through (i).

|     | T      | U      | V      |
|-----|--------|--------|--------|
| (a) | $CR_a$ | N      | $CHR_a$ |
| (b) | $CR_a$ | N      | $NR_b$ |
| (c) | $CR_a$ | N      | O      |
| (d) | N      | N      | O      |
| (e) | $CR_a$ | $CR_a'$ | $NR_b$ |
| (f) | $CR_a$ | $CR_a'$ | O      |
| (g) | N      | $CR_a'$ | $CHR_a$ |
| (h) | N      | $CR_a'$ | $NR_b$ |
| (i) | N      | $CR_a'$ | O      |

In this list $R_a$ and $R_a'$ are not OH or $NH_2$, N represents nitrogen and O represents oxygen. This cycloaddition provides products of the structure 10, wherein $R^1$ and $R^2$ are as defined above and B is an amino protecting group or hydrogen.

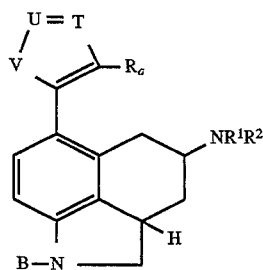

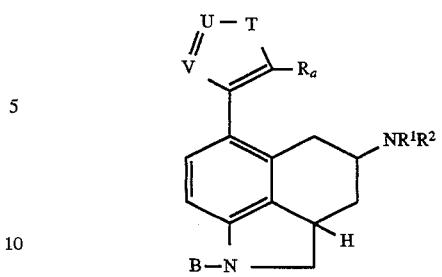

wherein $R^1$, $R^2$, $R_a$ and B are as defined above.

The 1-nitrogen of structures 8 and 10 can be protected using standard protecting groups preferably $(C_2H_5)_2NC(O)-$, triisopropylsilyl, benzoyl, or benzenesulfonyl.

Alternatively, the 6-alkyne-substituted indole of structure 8 can be reacted with a dipole of the type $^+T-U=V^-$ in which T, U, and V are selected from the following list for (j) and (k):

|     | T      | U | V |
|-----|--------|---|---|
| (j) | $CHR_a$ | N | N |
| (k) | $NR_b$ | N | N |

In this list $R_a$ is not OH or $NH_2$ and N is nitrogen. This reaction provides products of structure 12, Alternative procedures for preparing certain of the instant compounds are set forth hereinbelow in Schemes 2 through 19. As used in these reaction Schemes, "Ar" refers to the 1,2,2a,3,4,5-hexahydrobenz[cd]indole, with the indicated substituent in the 6-position. In these Schemes, "Me" is methyl, "Et" is ethyl, "NBS" represents n-bromosuccinimide, $R_a$, $R_b$, $R_c$ and $R_d$ are defined above, "MsCl" represents methanesulfonyl chloride, "$\Delta$" represents heat, "$\phi$" and "Ph" each represent phenyl, "DMF" represents dimethylformamide, "DMS" represents dimethyl sulfide, "TMS" represents trimethylsilyl, "[O]" represents an oxidant, Lawesson's reagent is p-methoxyphenyl-thionophosphine sulfide dimer, "Ac" represents acetyl, "NCS" represents N-chlorosuccinimide, "DCC" represents dicyclohexylcarbodiimide, "Im" represents 1-imidazolyl, and "[H]" represents a reductant. As set forth hereinabove, the 1-nitrogen of the benz[cd]indole is normally protected with an amino blocking group, preferably triisopropylsilyl.

Scheme 2

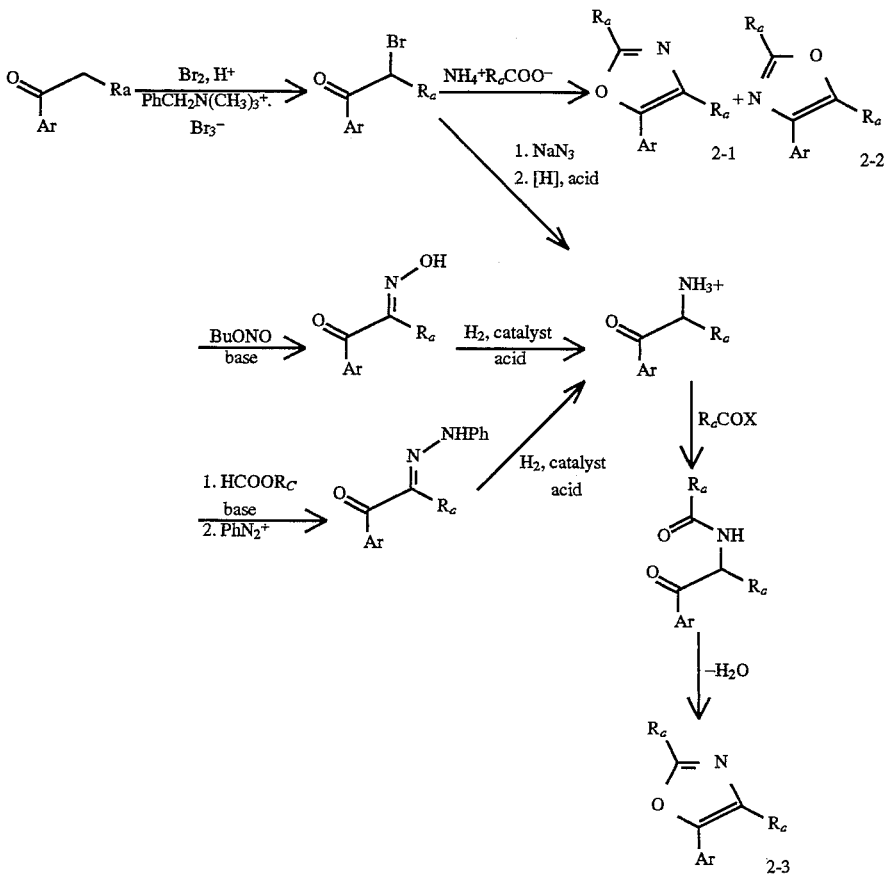

Scheme 3
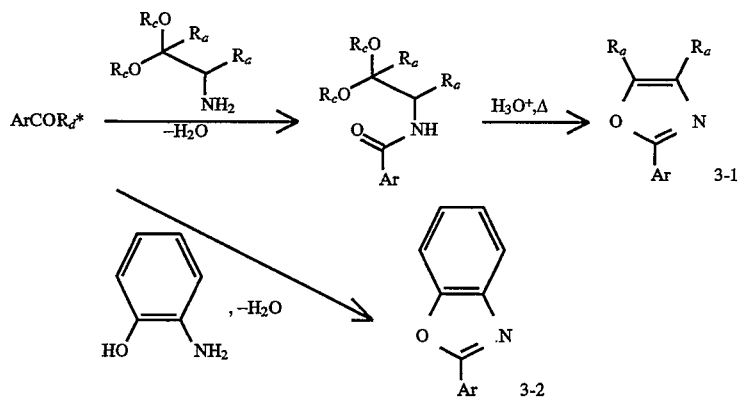
Scheme 4
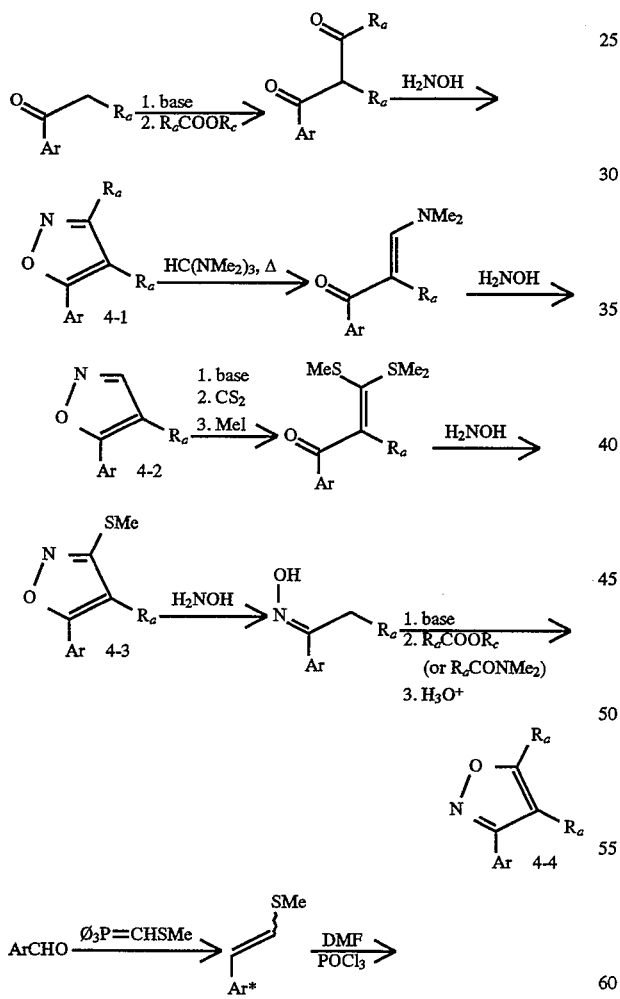

-continued
Scheme 4
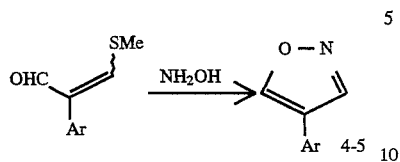
Scheme 5
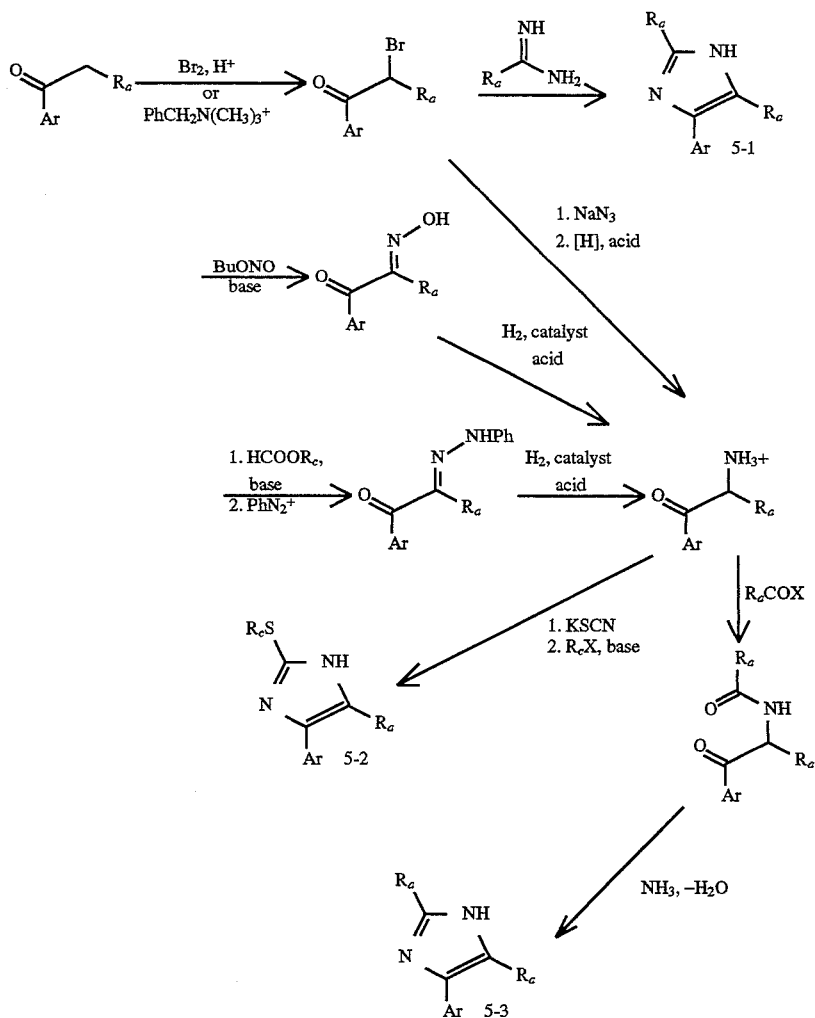
Scheme 6
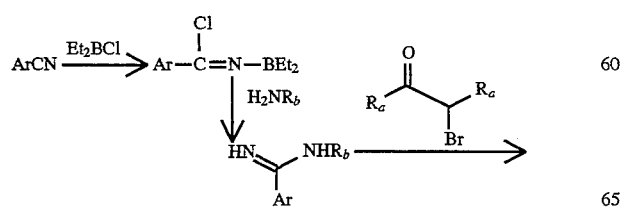
-continued
Scheme 6
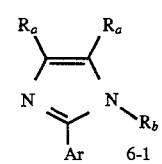

-continued
Scheme 6
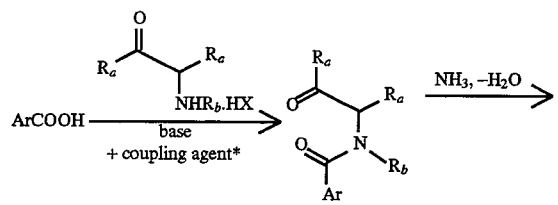
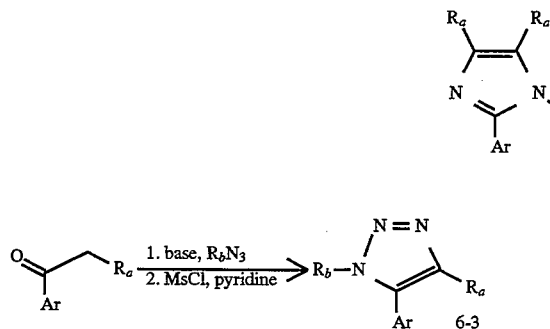
-continued
Scheme 6
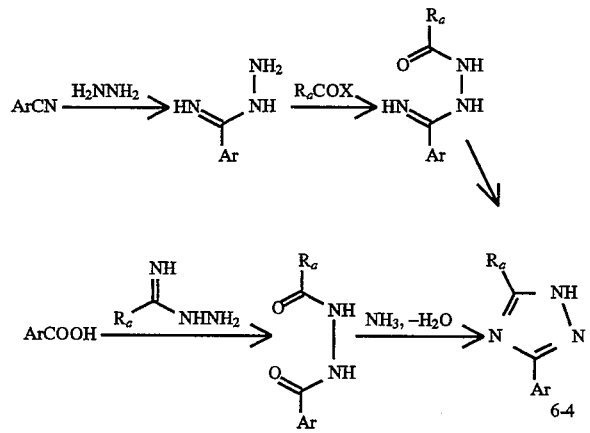
*For example, DCC or Im$_2$CO.
Scheme 7
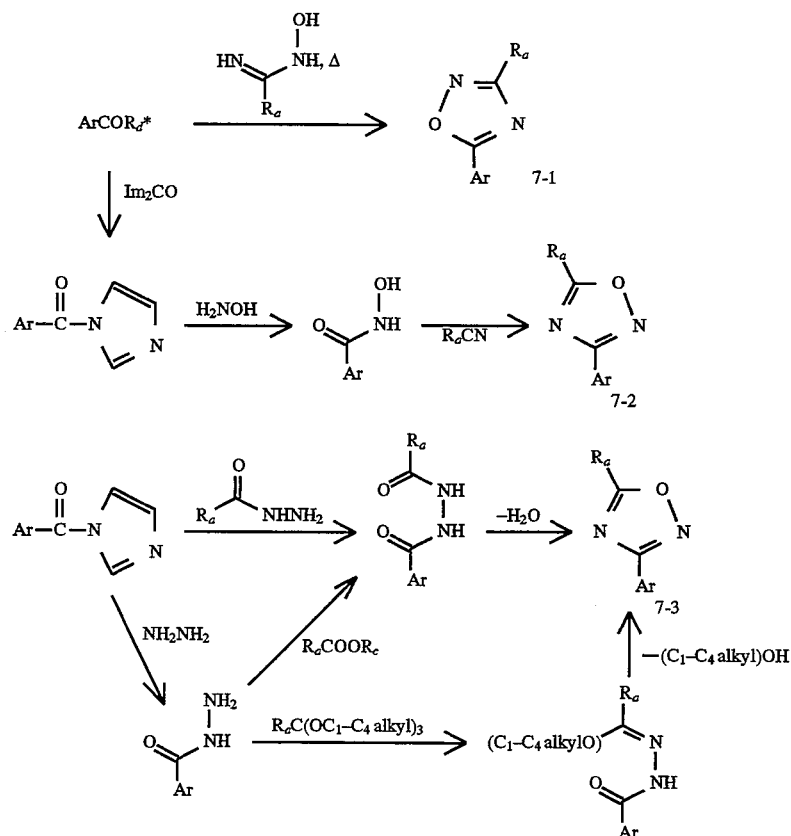
*When R$_d$ is OH a coupling agent, for example DCC or IM$_2$CO, is preferably also employed.

Scheme 8
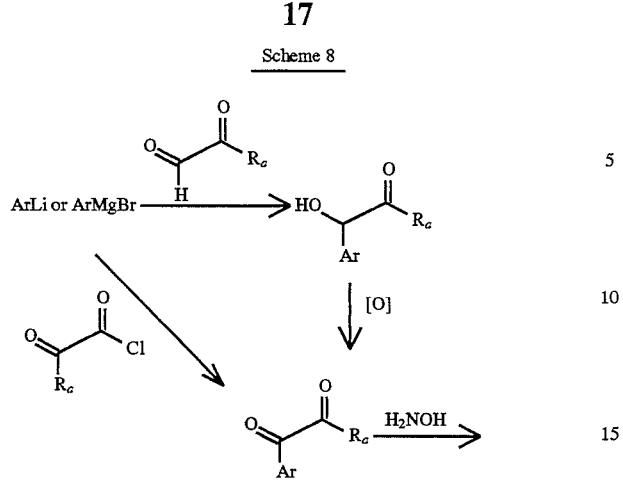
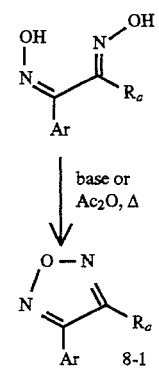
Scheme 9
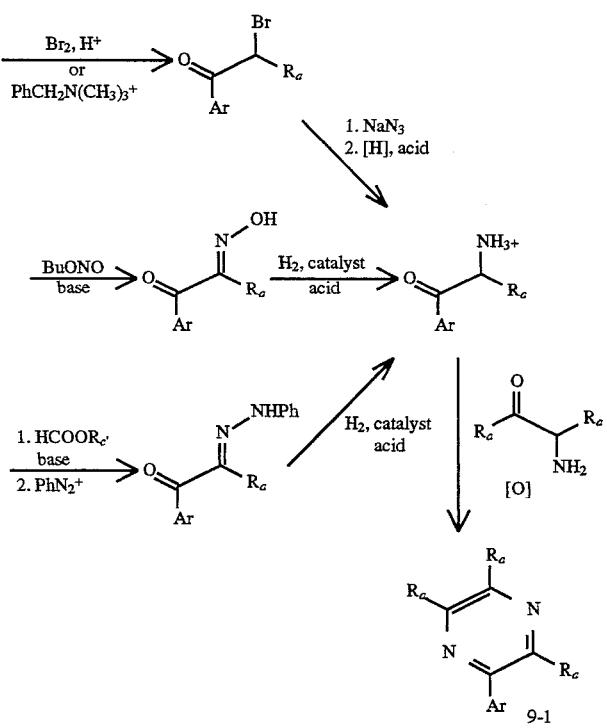

Scheme 10
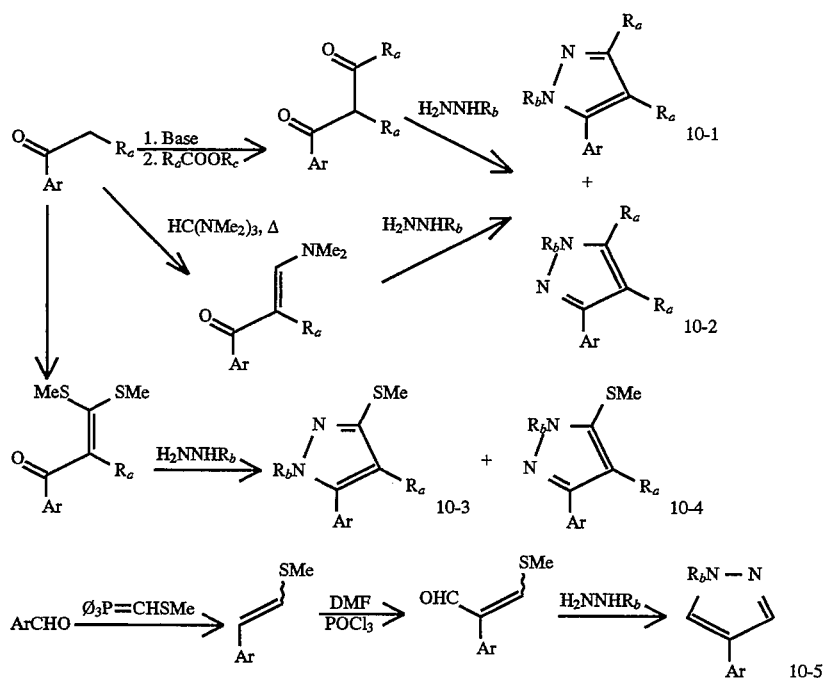
Scheme 11
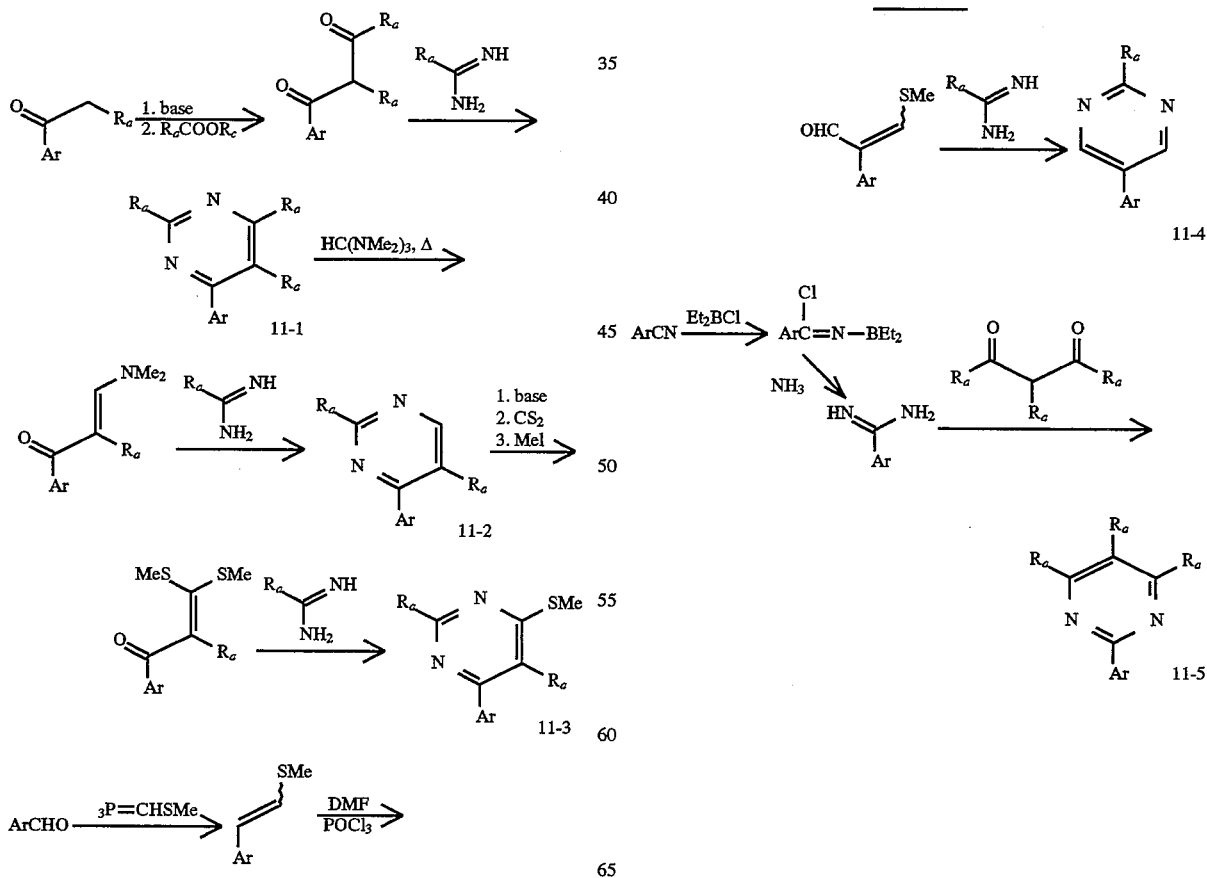

Scheme 12
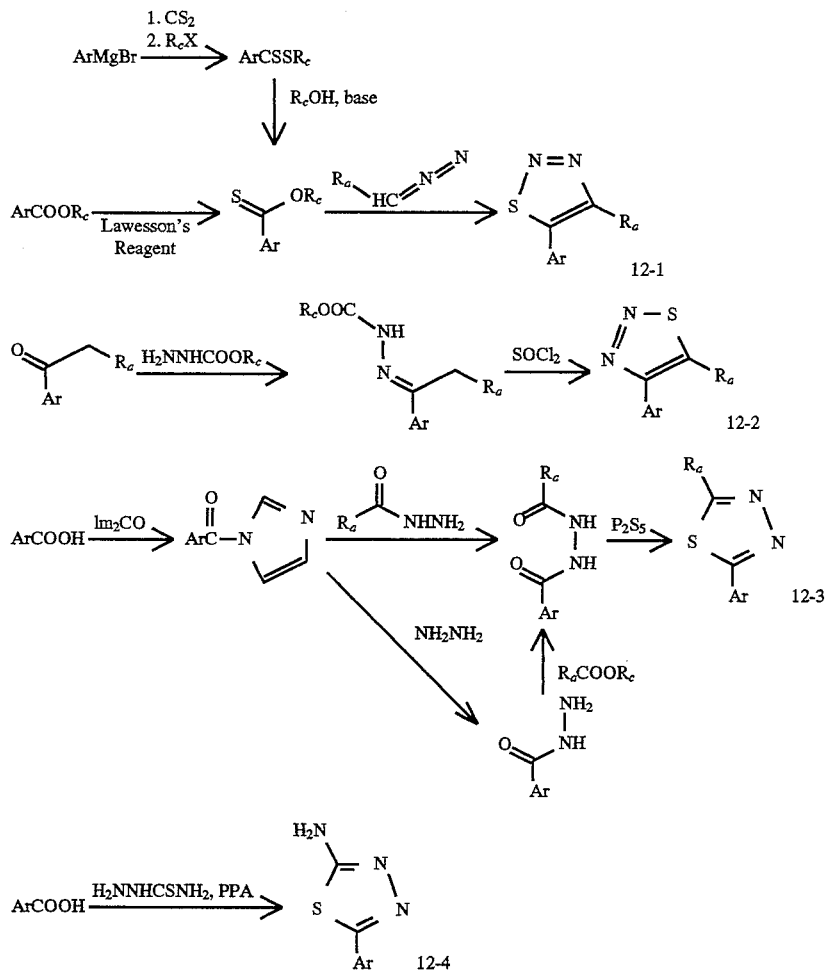
Scheme 13
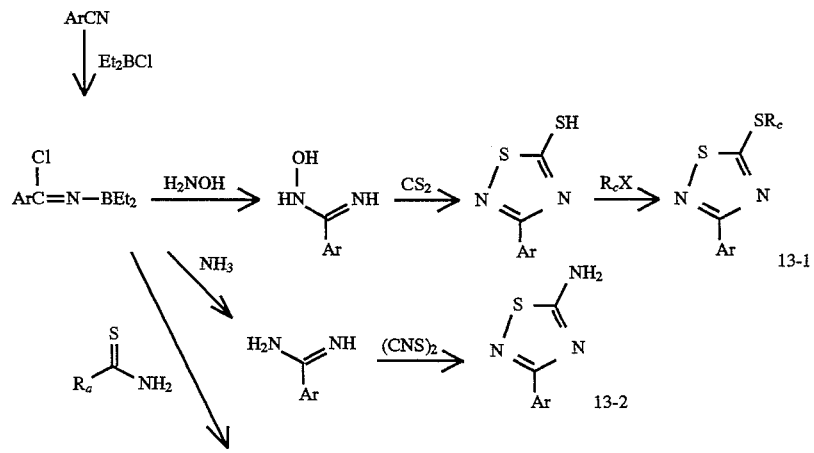

-continued
Scheme 13
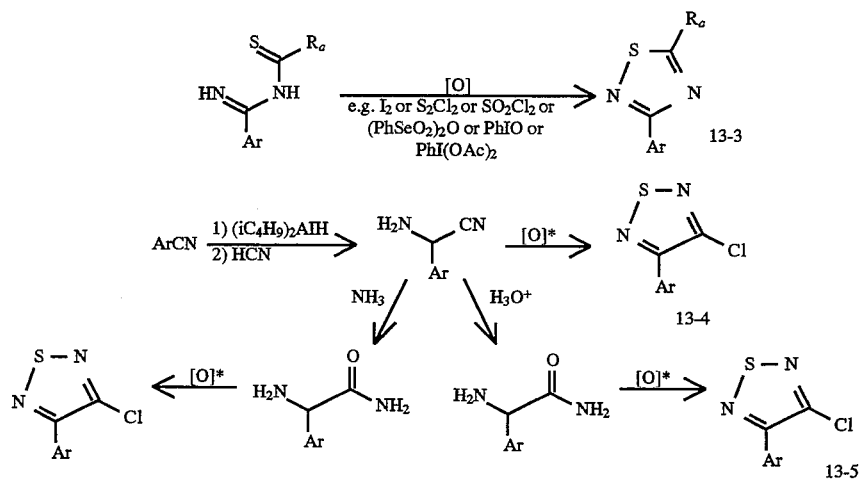
[O]*, e.g., SOCl₂ or SCl₂ or S₂Cl₂ or SO₂Cl₂
Scheme 14
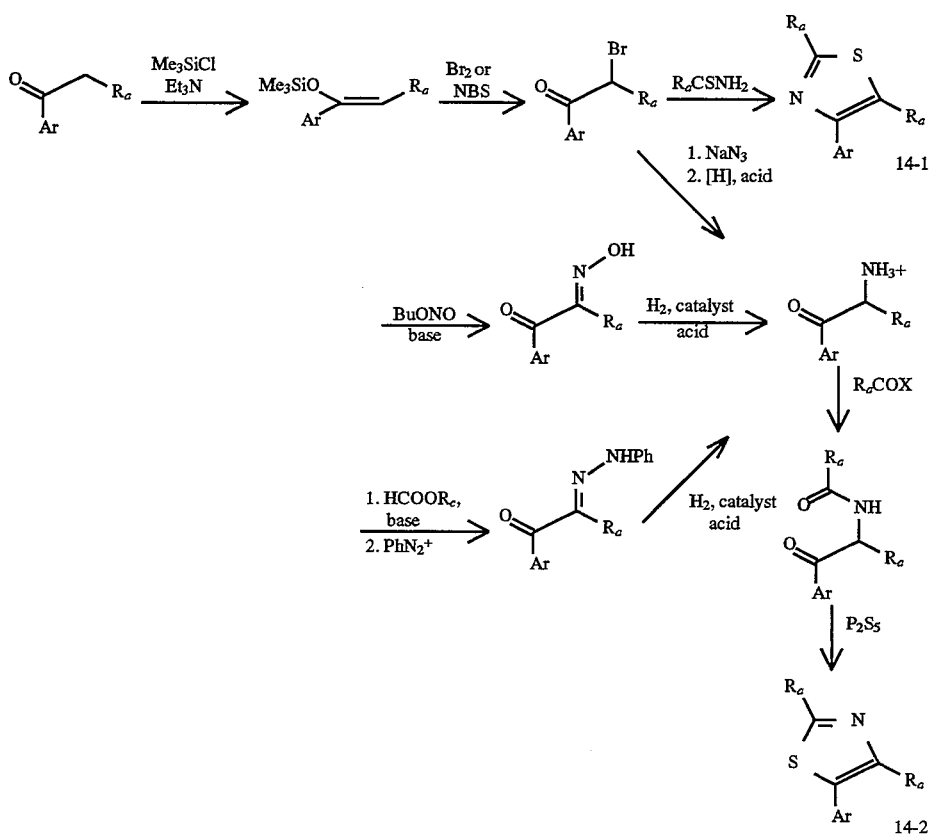

Scheme 15
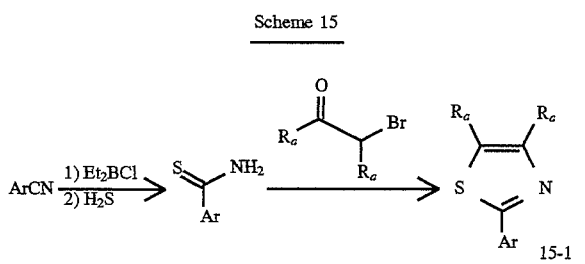
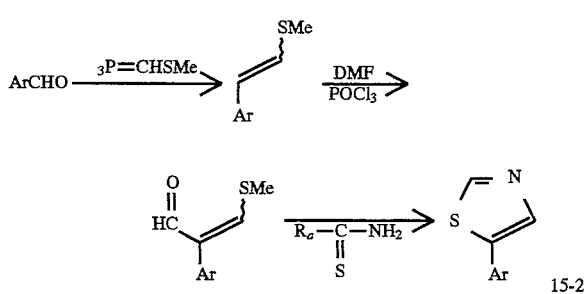
Scheme 16
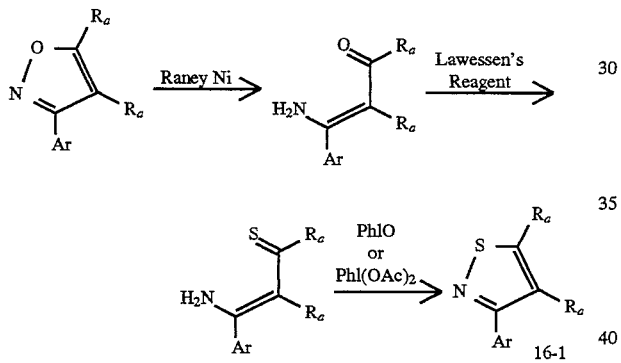
-continued
Scheme 16
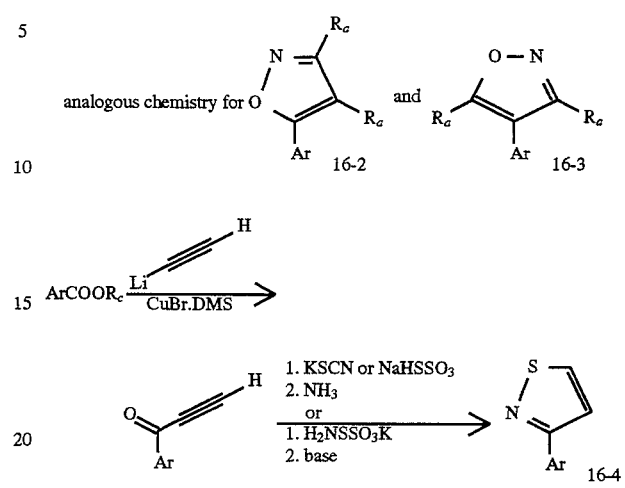
Scheme 17
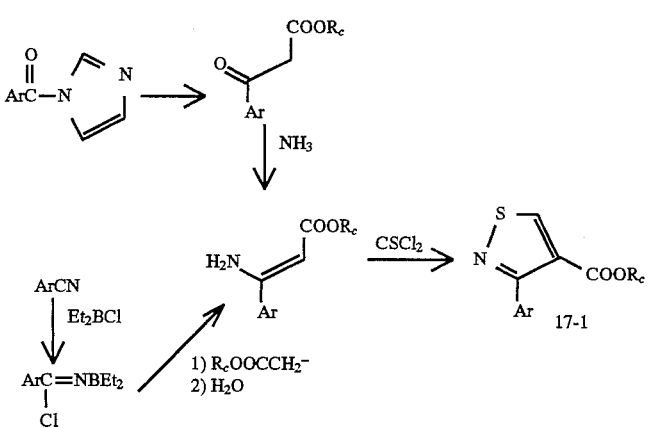

-continued
Scheme 17
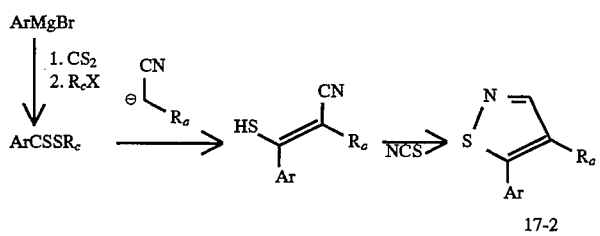
Scheme 18
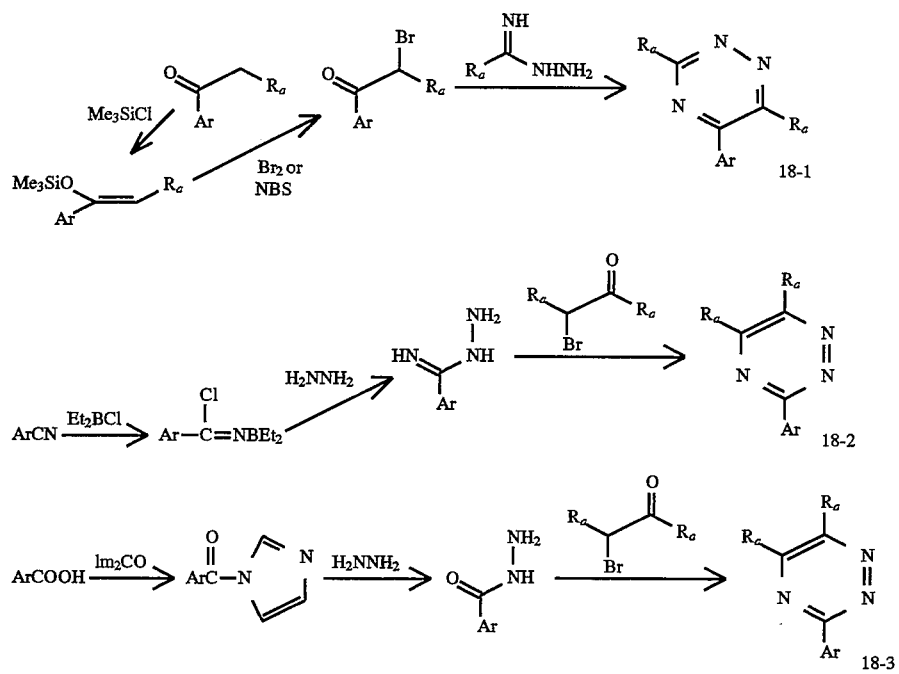
Scheme 19
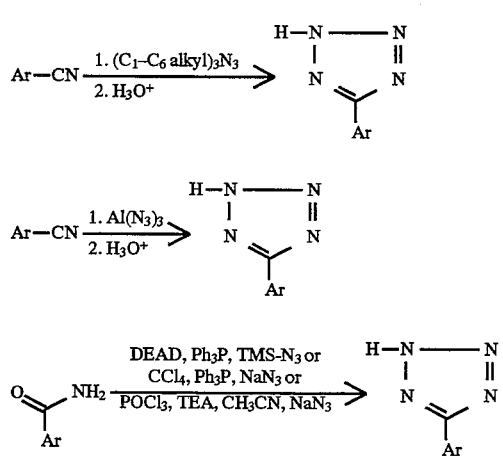
-continued
Scheme 19
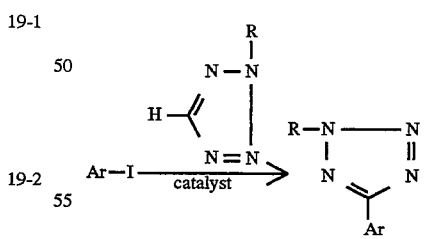
Scheme 20 illustrates a preparation of a starting material for reaction Scheme 1.

Scheme 20

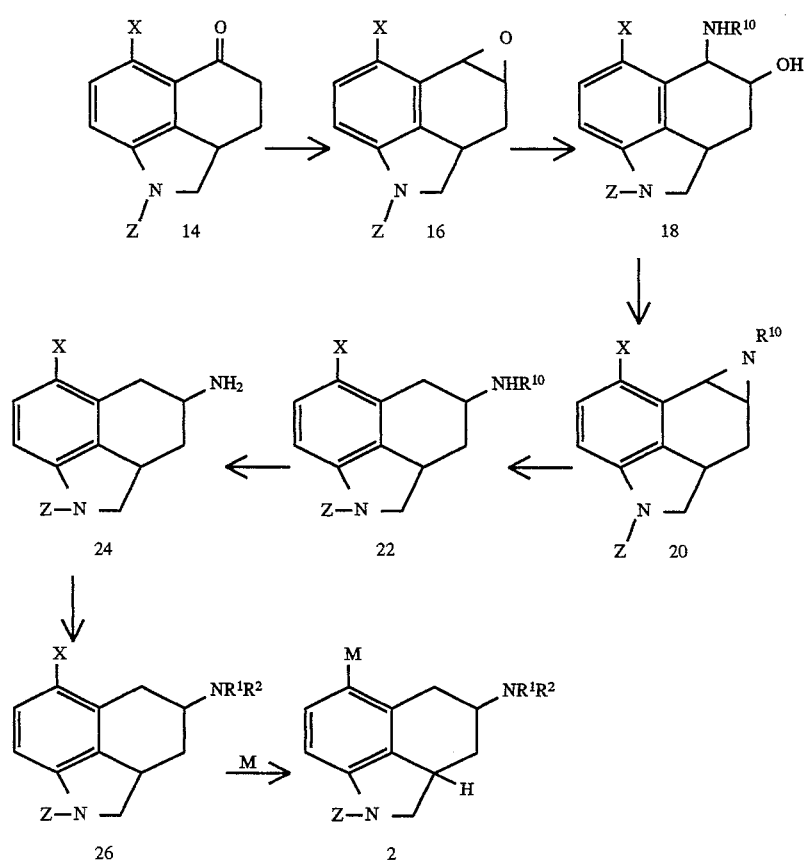

In scheme 20, epoxides of Formula 16 are known to the art or can be prepared from compounds known to the art using common reagents and techniques. For example, Flaugh, et al., *J. Med. Chem.*, 31, 1746 (1988); Nichols et al., *Org. Prep. and Proc., Int.*, 9, 277 (1977); and Leanna et al., *Tet. Lett.*, 30, No. 30, 3935 (1989), teach methods of preparation of various embodiments of compounds of structures 16. Those skilled in the art of organic chemistry will recognize that there are four stereoisomers of structure 16:

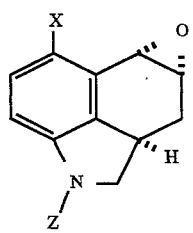

16a

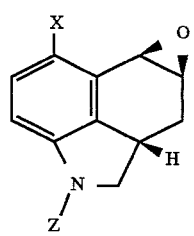

16b

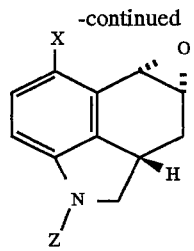

16c

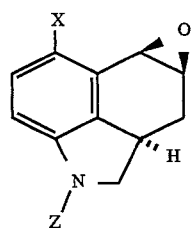

16d

Structures 16a and 16b are herein referred to collectively as the exo-isomers; similarly, structures 16c and 16d are the endo-isomers. Leanna et al., supra, teach the preparation of epoxides of structures 16 which are substantially exo or substantially endo, as desired. The preferred starting material is the compound of structure 16 wherein Z is benzoyl and X is hydrogen; the most preferred starting material is the mixture of substantially the exo-isomers thereof.

Amino alcohols of structure 18 are formed by reacting an epoxide of structure 16 with an amine of formula $R^{10}NH_2$. Such amines are readily available. Opening of the epoxide ring proceeds substantially regiospecifically with the amino group at the 5-position and the hydroxyl group at the 4-position. The reaction is also stereospecific in the sense that stereoisomers of structure 18a–d are formed from, respectively, stereoisomers of structure 16a–d,

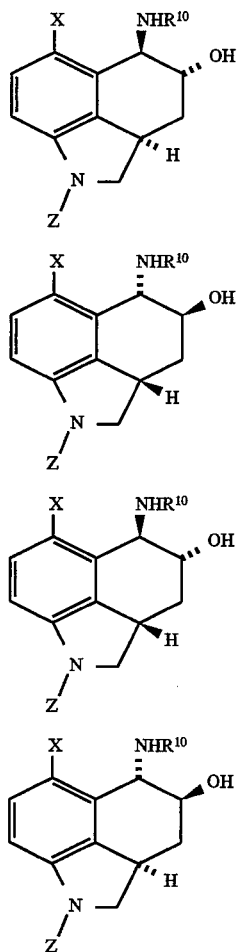

A stereoselective synthesis of the amino alcohol of structure 18, and hence of all the subsequent intermediates and products of Scheme 20, can be effected by using a substantially pure enantiomer of an amine of the formula $R^{10}NH_2$ wherein $R^{10}$ contains at least one chiral center. The diastereomers of the resulting amino alcohol can then be separated by a number of means known in the art, for example by chromatography or crystallization. Suitable solvents for recrystallization include those such as diethyl ether, n-butanol, and mixtures of hexane and ethyl acetate. An alternative method of achieving a stereospecific synthesis is depicted in Scheme 20 and comprises conversion of all the diastereomers of structure 18 to corresponding diastereomers of structure 20, followed by the separation of said diastereomers of structure 20; that alternative method is discussed below. If a stereoselective synthesis is not desired, then separation of the stereoisomers of the amino alcohol of structure 18 is not required and the amine $R^{10}NH_2$ need not be optically active.

A particularly efficient stereoselective process for a highly preferred compound of structure 18, 1-benzoyl-4-hydroxy-5-(1-phenylethyl)amino-1,2,2a,3,4,5-hexahydrobenz[cd] indole, comprises the reaction of a mixture of substantially the exo-isomers of the corresponding epoxide of structure 16, or a mixture of substantially the endo-isomers of the corresponding epoxide of structure 16, with a substantially pure enantiomer of 1-phenethylamine in the solvent n-butanol and the subsequent selective crystallization of one of the two isomers of the amino alcohol. The temperature of the reaction can be from about 50° to about 150° C., preferably about 80° to about 100° C.

After the reaction is complete, as determined for example by thin layer chromatography or liquid chromatography, the desired amino alcohol is crystallized at about –20° to about 40° C.; the preferred temperature for the crystallization is about 0° to about 15° C. Therefore this process has the valuable attribute that the reaction and the separation of stereoisomers occur efficiently in a single step. By the proper selection of the epoxide isomers, exo or endo, and the enantiomer of 1-phenylethylamine, R or S, one can determine which of the stereoisomers of the compound of structure 18 precipitate from the reaction mixture.

A number of methods of forming aziridines such as those of structure 20 from amino alcohols such as those of Formula 18 are known to the art. Two examples are the use of diethyl azodicarboxylate and triphenylphosphine (O. Mitsunobu, Synthesis, January, 1981, page 1), and the use of bromine and triphenylphosphine (J. P. Freemer and P. J. Mondron, Synthesis, December, 1974, page 894).

A particularly efficient alternative to the above methods involves treating a compound of structure 18 with a tertiary amine in an inert solvent followed by the addition of methanesulfonyl chloride. The following stereoisomers of the aziridine of structure 20, 20a–d, arise respectively from the stereoisomers of structure 18a–d, with retention of configuration at any chiral center in the substituents Z, $R^{10}$ or X:

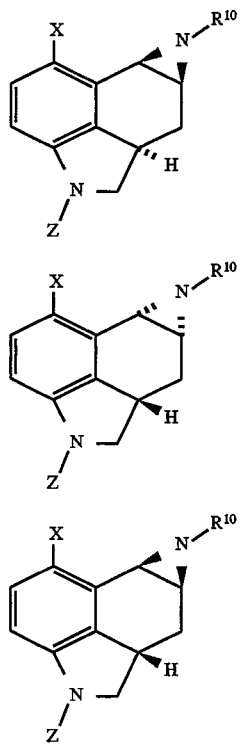

-continued

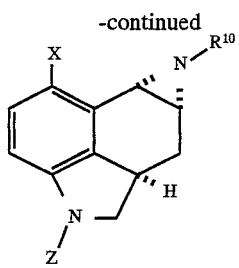

20d

Suitable tertiary amines are those of the formula $(R^{11})_3N$, where the $R^{11}$ groups are independently $C_1$–$C_4$ alkyl. Suitable solvents are chlorinated hydrocarbons such as methylene chloride, chloroform, carbon tetrachloride, and dichloroethane; aromatic hydrocarbons such as benzene, toluene, and the xylenes; and ethers such as tetrahydrofuran, diethyl ether, and methyl t-butyl ether. The reaction can be conducted at a temperature from about −35° to about 45° C. In the preferred embodiment, the amino alcohol is treated with triethylamine in methylene chloride at about −20° to about 0° C., then the reaction mixture is warmed to about 15° to about 35° C. for the completion of the reaction. If desired, the product, an aziridine of structure 20, can be crystallized from an appropriate solvent such as acetonitrile or isopropanol after an aqueous workup. In the event that Z contains at least one chiral center in substantially a single stereoconfiguration and that the aziridine of structure 20 is prepared as a mixture of stereoisomers, said stereoisomers can be separated by methods such as chromatography and crystallization, thereby providing a stereospecific synthesis of the aziridine of structure 20 and subsequent products.

The aziridine ring can be opened to form an intermediate secondary amine of structure 22. A number of methods of opening aziridines are commonly known. It is, however, crucial that the method used for opening the aziridine to form a secondary amine of structure 22 be substantially regiospecific; the aziridine must be opened to form substantially the 4-amino compound rather than the 5-amino compound. One such method is catalytic hydrogenolysis as taught by Y. Sugi and S. Mitsui, *Bull. Chem. Soc. Jap.*, 43, pp. 1489–1496 (1970). Catalysts which are suitable are the usual hydrogenation and hydrogenolysis catalysts, such as the noble metal catalysts; the preferred catalyst is palladium. Suitable solvents include hydrocarbons such as hexanes and heptanes; aromatic hydrocarbons such as benzene, toluene, xylenes, ethylbenzene, and t-butylbenzene; alcohols such as methanol, ethanol, and isopropanol; and mixtures of solvents such as acetic acid mixed with said alcohols. The preferred solvent for preparing the compound of structure 22, wherein Z is benzoyl, X is hydrogen, and $R^{10}$ is 1-phenylethyl, is a mixture of tetrahydrofuran and phosphoric acid or acetic acid. The source of hydrogen can be an atmosphere of elemental hydrogen supplied at a pressure of about 1 atmosphere or higher, or the source of hydrogen can be compounds which are suitable to serve as hydrogen donors in a catalytic transfer hydrogenolysis reaction, such as formic acid, hydrazine, or cyclohexene. The preferred hydrogen source is an atmosphere of hydrogen gas supplied at about 1 to about 10 atmospheres pressure. The temperature of the reaction may be from about −20° to about 80° C.; the preferred temperature for the hydrogenolysis of the aziridine wherein Z is benzoyl, X is hydrogen, and $R^{10}$ is 1-phenylethyl is about −20° to about 0° C.

The conversion of compounds of structure 20 to compounds of structure 22 proceeds without disturbing the stereochemical configuration of the chiral centers at the 2a- or 4-positions of the structure 22 or of the chiral centers that may be present in any of the substituents.

If desired, the compound of structure 22 can be isolated by the usual methods such as crystallization. The secondary amine of structure 22 can be converted to a primary amine of structure 24 by a number of methods known to the art of organic chemistry, or alternatively the secondary amine itself can be isolated.

However, the preferred method is to convert the secondary amine of structure 22 to the primary amine of structure 24 without isolating the secondary amine, but rather by simply continuing without interruption the hydrogenolysis reaction that produced the compound of structure 22. Therefore, the preferred solvent and catalyst are the same as those for the preparation of the secondary amine of structure 22. It may be desirable to conduct the hydrogenolysis of the secondary amine of structure 22 at a different temperature or a different pressure or different temperature and pressure than the hydrogenolysis of the aziridine of structure 20. For the hydrogenolysis of the preferred compound of structure 22 wherein Z is benzoyl, X is hydrogen, and $R^{10}$ is 1-phenylethyl, the preferred temperature and pressure are about 50° to about 60° C. and about 1 to about 20 atmospheres. Under these conditions the hydrogenolysis of compounds of structure 22 to compounds of structure 24 proceeds without disturbing the stereochemical configuration of the chiral center at the 4-postion.

The isolation of the compound of structure 24 can be accomplished by the usual methods such as crystallization. If desired, the compound of structure 24 can be further purified, for example by recrystallization.

Of course, as those skilled in the art will recognize, variations of Scheme 20 will be desirable or necessary for certain embodiments of the invention. For example, it may be undesirable to subject a compound in which X is halo to the catalytic hydrogenolysis steps of Scheme 20 because the undesired displacement of the halogen may compete with the desired hydrogenolysis of the carbon-nitrogen bonds. One alternative strategy is to postpone the halogenation until after the hydrogenolysis. Another alternative strategy is to use a milder means of reduction that would leave the halogen in place. A third alternative, useful in the instance when the halogen is to serve as a leaving group, is to perform the desired displacement of halogen before the hydrogenolysis step.

Compounds of Formula 1 can be prepared from the compound of structure 24, whether it exists as a mixture of stereoisomers or as a substantially pure enantiomer, using common reagents and methods well known in the art. A preferred intermediate to the compounds of the instant invention is the 6-bromo-derivative. Preferably Z is an amino blocking group such as benzoyl. A preferred method of introducing the bromo substituent at the 6-position is by reaction with bromine in glacial acetic acid, buffered with sodium acetate. Amino blocking groups can be added, if desired, to the 4-amino substituent using such methods as those disclosed by Greene, supra, and Barton, supra. Alkyl groups can be added, if desired, to the 4-amino substituent using such common methods as ammonolysis of the appropriate halide as discussed by Morrison and Boyd, Chapter 22, *Organic Chemistry*, Third Edition, Allyn and Bacon, Boston, 1973, to provide a compound of structure 26 wherein $R^1$ and $R^2$ are defined hereinabove. If desired, the benzoyl group can be removed from the 1-position using known methods and optionally replaced with other amino-protecting groups. Preferably the benzoyl group represented by Z is replaced with a triphenylmethyl group prior to the metallating step to form structure 2. The amino-protecting groups and alkyl groups can be added either before or after the bromination, as desired.

The 4-amino-6-bromohexahydrobenz[cd]indole starting materials used to prepare the compounds of the invention can be readily prepared by other processes such as depicted in Reaction Scheme 2 disclosed in U.S. Pat. No. 4,576,959 of Flaugh, incorporated herein by reference in its entirety.

The procedure of Scheme 20 using the 4,5-epoxide provides a convenient way to prepare the optically active isomers of the compounds of the present invention. Such isomers can also be isolated by resolving racemic mixtures. This resolution can be carried out in the presence of a resolving agent, by chromatography or by repeated crystallization. Particularly useful resolving agents are d- and l-tartaric acids, d- and l-ditoluoyltartaric acids, and the like.

The methods of preparation described in Schemes 2–19 provide compounds in which the heteroaromatic ring may or may not be substituted. The general reactions provided below set forth methodology for incorporating, interconverting, and removing substituents on the heteroaromatic ring. Additional methods for performing these transformations are cited in *Comprehensive Organic Transformations* by Richard C. Larock, VCH Publishers, Inc., New York (1989) which is incorporated herein by reference. "HET" refers to the heteroaromatic attached to the hexahydrobenz[cd]indole at position C-6.

1. Halogen substituent (X):

HET—OH ⟶ HET—X    POX$_3$, PX$_3$, SOX$_2$, PPh$_3$.X$_2$, or P(OR)$_3$.X$_2$

HET—NH$_2$ ⟶ HET—X    1. HONO; 2. CuX, or KI, or HBF$_4$, Δ

2. O(C$_1$–C$_3$ alkyl), i.e., [OR]

HET—X ⟶ HET—OR    RO—, CuI, (DMF, or DMAc, or NMP), Δ

HET—OH ⟶ HET—OR    Base, RX; or CH$_2$N$_2$

3. Hydroxy substituent:

HET—NH$_2$ ⟶ HET—OH    1. HONO; 2. H$_3$O$^+$, Δ

HET—OMe ⟶ HET—OH    48% HBr, Δ; or BBr$_3$

4. Cyano substituent:

HET—NH$_2$ ⟶ HET—CN    1. HONO; 2. CuCN

HET—X ⟶ HET—CN    CuCN, (DMF, or DMAc, or NMP), Δ; or CN$^-$, Δ

5. S(C$_1$–C$_3$ alkyl), i.e, [SR]

HET—NH$_2$ ⟶ HET—SR    1. HONO; 2. RSH, base

HET—X ⟶ HET—SR    RS$^-$, CuI, (DMF, or DMAc, or NMP), Δ

6. Amino substituent:

HET—NO$_2$ ⟶ HET—NH$_2$    H$_2$, catalyst (i.e., Pt or Pd)

7. Hydrogen substituent:

HET—X ⟶ HET—H    H$_2$, catalyst; or R$_3$SnH, 2, 2'-azobis (2-methyl)-propionitrile), Δ

HET—OH ⟶ HET—H    1. 5-chloro-1-phenyltetrazole, 2. H$_2$, catalyst

HET—NH$_2$ ⟶ HET—H    1. HONO, 2. H$_3$PO$_2$

HET—CH$_2$Ph ⟶ HET—H    H$_2$, catalyst (i.e., Pd) (This applies if the benzyl group is attached to a nitrogen in the heterocyclic ring.)

HET—SR ⟶ HET—H    Raney Ni 6-acyl-substituted-hexahydrobenz[cd]indoles are preferred intermediates in the preparation of certain of the compounds of the instant invention, particularly 6-isoxazole-indoles and 6-pyrazole-indoles. The 6-acyl substituted indolines can be prepared by several routes using the 6-iodo-substituted indolines of structure 30 as depicted in Scheme 21 where R$^1$, R$^2$ and Z are as defined hereinabove.

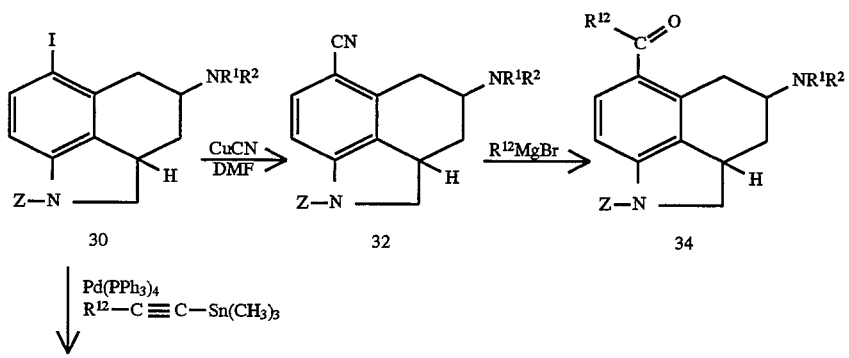

Scheme 21

-continued
Scheme 21

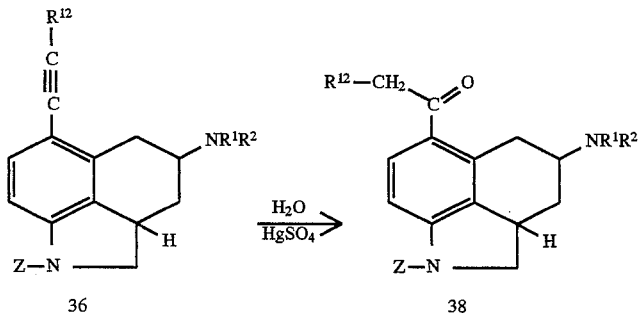

In a preferred method of preparation as depicted in Scheme 21, the nitrile 32 is contacted with an organometallic reagent such as a Grignard reagent under standard conditions to provide the 6-acyl derivative 34. For this reaction Z is preferably benzoyl or trityl. Alternatively, a 6-alkyne intermediate of structure 36 can be prepared and then hydrolyzed to provide the acyl derivative 38. This method provides a methylene group adjacent to the carbonyl group. In this method Z can be an amino protecting group such as benzoyl although the unprotected 1-nitrogen is preferred, i.e., Z is hydrogen. Compounds of structure 30 can be contacted with a palladium catalyst $Pd(PPh_3)_4$ [where Ph is phenyl] and the tin alkyne compound $R^{12}$-C≡C-Sn$(CH_3)_3$ wherein $R^{12}$ is a $C_1$-$C_7$ alkyl, substituted $C_1$-$C_7$ alkyl, aryl ($C_1$-$C_3$ alkyl), substituted aryl ($C_1$-$C_3$ alkyl), or $C_3$-$C_7$ cycloalkyl. This reaction is normally conducted in a solvent such as toluene at an elevated temperature, for example at about 100° C. Typically an excess of the tin alkyne is used along with about 0.25 equivalents of the palladium compound based on compound 30. The 6-alkyne 36 is then contacted with $HgSO_4$ in water to provide the ketone 38.

In another preparation method depicted in Scheme 22, the 6-iodo derivative 30 can be used to prepare certain 6-acyl compounds directly. This is accomplished by contacting the 6-iodo compound with a trialkyltinalkyl complex and carbon monoxide in the presence of a palladium catalyst $Pd(PPh_3)_4$ [where Ph is phenyl] as described in the literature for arylhalides. [A. Schoenberg and R. F. Heck, *J. Org. Chem.*, 39, p. 3327 (1974); and A. Schoenberg, I. Bartoletti, and R. F. Heck, *J. Org. Chem.*, 39, p. 3318 (1974)]. Although a blocking group Z such as diethylcarbamoyl can be used for this method, the method can also be accomplished when Z is hydrogen, or the blocking group can be removed to provide compounds of structure 40 where $R^1$, $R^2$ and $R^{12}$ are as defined above.

Scheme 22

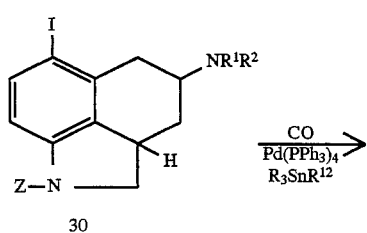

-continued
Scheme 22

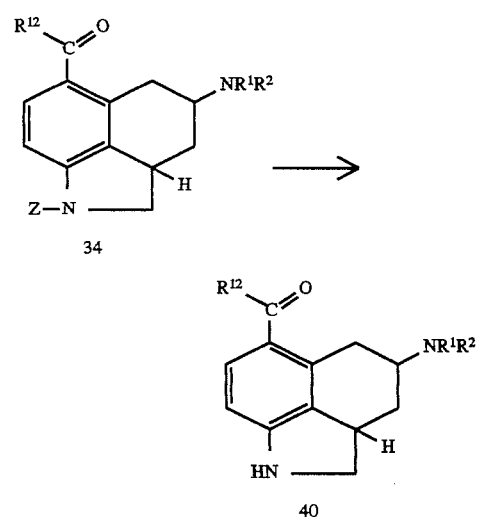

The following examples further illustrate the preparation of the compounds of this invention. The examples are provided for purposes of illustration only and are not to be construed as limiting the scope of the instant invention in any way.

The terms and abbreviations used in the instant examples have their normal meaning unless otherwise designated, for example, "°C." refers to degrees celsius; "N" refers to normal or normality; "mmol" referes to millimole; "g" refers to gram; "mL" means milliliter; "M" refers to molar; "min" refers to minutes; "hr" refers to hours; "NMR" refers to nuclear magnetic resonance; and "MS" refers to mass spectrometry.

EXAMPLE 1

A. Preparation of (±)-1-Benzoyl-6-cyano-4-(di-n-propylamino)-1,2,2a,3,4,5-hexahydrobenz[cd]indole To a solution of (±)-1-benzoyl-6-bromo-4-(di-n-propylamino)hexahydrobenz[cd]indole (5.5 g, 12.5 mmol) in DMF (100 mL) under a $N_2$ atmosphere was added 3.4 g (37.5 mmol) of CuCN and 7.1 g (37.5 mmol) of CuI. The reaction mixture was then stirred at 140° C. for 6 hr. The reaction mixture was poured onto ice, diluted with water, $CH_2Cl_2$ added and stirred for 30 minutes. The mixture was filtered through a Celite pad and the filtrate was extracted twice with $CH_2Cl_{12}$. The organic solution was washed twice with saturated NaCl solution. The $CH_2Cl_2$ solution was dried over MgSO$_4$ and then evaporated to provide 4 g of a solid. Chromatography of this crude product over silica gel with 1:19 MeOH/CH$_2$Cl$_2$ as eluent gave 3 g (62%) of product.

mp=122°–124° C.

B. Preparation of (−)(2aS,4R)-1-Benzoyl-6-cyano-4-di-n-propylamino)-1,2,2a,3,4,5-hexahydrobenz[cd]indole.

To a solution of (−)(2aS,4R)-6-bromo compound (30.0 g; 0.068 mol) in 500 ml of DMF was added CuCN (18.3 g; 0.2 mol) and CuI (38.0 g; 0.2 mol). The reaction mixture was then stirred at 140° C. for 6 hr. The reaction mixture was poured into 4L of water. The precipitate was collected and washed several times with water. The precipitate was suspended in dilute NH$_4$OH and slurried with ethyl acetate. The whole mixture was filtered through a celite pad. The ethyl acetate solution was separated and washed with brine solution. The ethyl acetate solution was dried (MgSO$_4$) and concentrated to dryness to provide 21.3 g of the (−)-6-nitrile.

C. Preparation of the (+)(2aR,4S)-6-cyano counterpart of Example 1B.

In a similar manner as in Example 1B above, the (+)(2aR,4S)-6-bromo compound (17.1 g, 0.039 mol) was contacted with CuCN (10.75 g; 0.12 mol) and CuI (22.8 g; 0.12 mol) in 300 ml DMF to give 11.6 g of (+)-6-cyano compound.

EXAMPLE 2

Preparation of (±)-6-cyano-4-(di-n-propylamino)-1,2,2a,3,4,5-hexahydrobenz[cd]indole.

To a stirred solution of 4.8 g (0.0124 mol) of (±)-1-benzoyl-6-cyano-4-(di-n-propylamino)-1,2,2a,3,4,5-hexahydrobenz[cd]indole in 200 mL of THF cooled to −78° C. under a N$_2$ atmosphere were added 16 mL (0.025 mol) of a 1.6M solution of n-butyl lithium in hexane. The reaction mixture was stirred at −78° C. for 30 minutes and then allowed to warm to −20° C. To the reaction mixture was added 100 mL of 1N HCl. The mixture was extracted once with ethyl ether. The acidic solution was made alkaline with the addition of cold 5N NaOH. The basic mixture was extracted twice with CH$_2$Cl$_2$. The combined organic solution was washed with a saturated NaCl solution. The CH$_2$Cl$_2$ solution was dried over MgSO$_4$ and evaporated to give 4 g of an oil. Chromatography of this oil over silica gel with ethyl acetate as eluent gave 3 g (85%) of product as an oil which upon standing solidified.

EXAMPLE 3

Preparation of (+)(2aS,4R)-1-trityl-6-cyano-4-(di-n-propylamino)-1,2,2a,3,4,5-hexahydrobenz[cd]indole.

To a solution of (+)(2aS,4R)-6-cyano-4-(di-n-propylamino)-1,2,2a,3,4,5-hexahydrobenz[cd]indole (12.8 g, 0.045 mol) and triethylamine (4.5 g, 0.045 mol) in 400 mL of methylene chloride was added a solution of triphenylmethyl chloride (trityl chloride) (12.6 g, 0.045 mol) in 100 mL of methylene chloride dropwise at room temperature. The reaction mixture was stirred for 16 hr at room temperature. The reaction mixture was extracted with water and cold 1N HCl. The organic solution was washed with a saturated NaHCO$_3$ solution and with a saturated brine solution. The organic layer was dried (MgSO$_4$) and concentrated to dryness in vacuo to give a residue. The residue was slurried with warm hexanes, cooled and filtered to remove insolubles. The filtrate was concentrated to an oil. The oil was chromatographed (silica gel, 20% ethyl acetate in hexanes) to provide 20.6 g of the (+)-trityl nitrile.

EXAMPLE 4

Preparation of (+)(2aS,4R)-6-acetyl-4-(di-n-propylamino)-1,2,2a,3,4,5-hexahydrobenz[cd]indole.

A solution of 2.4 g (4.6 mmol) of (+)(2aS,4R)-1-trityl-6-cyano-4-(di-n-propylamino)-1,2,2a,3,4,5-hexahydrobenz[cd]indole in 100 mL of THF was treated with 25 mL of 2.0M methylmagnesium bromide in diethyl ether. The reaction mixture was refluxed for 16 hr. The reaction mixture was cooled and excess Grignard reagent was decomposed with addition of a saturated NH$_4$Cl solution. The reaction mixture was extracted with ethyl acetate. The organic solution was evaporated to an oil. The oil was dissolved in 25 mL of 5N HCl and the solution was stirred at room temperature for 30 min. The acidic solution was made alkaline with the addition of excess concentrated NH$_4$OH solution. The basic mixture was extracted twice with ethyl acetate. The combined organic solution was washed once with a saturated NaCl solution and dried over MgSO$_4$. The ethyl acetate solution was evaporated to yield 1.4 g of an oil. Chromatography of this oil over silica gel with ethyl acetate as eluent gave 1.2 g (87%) of product. Recrystallization from hexanes yielded 840 mg of the product (+) ketone.

mp=121°–122° C. $[\alpha]_D$+67.40° (MeOH).

EXAMPLE 5

Preparation of (±)-6-acetyl-4-(di-n-propylamino)-1,2,2a,3,4,5-hexahydrobenz[cd]indole.

A solution of 0.5 g (1.8 mmol) of (±)-6-cyano-4-(di-n-propylamino)-1,2,2a,3,4,5-hexahydrobenz[cd]indole in 75 mL of benzene was treated with 5 mL of 2.0M methylmagnesium bromide in diethyl ether. The reaction mixture was refluxed for 2 days. The reaction mixture was cooled and excess Grignard reagent was decomposed with addition of a saturated NH$_4$Cl solution. The benzene layer was separated and washed once with a saturated NaCl solution. The organic solution was evaporated to an oil. The oil was dissolved in 25 mL of 5N HCl and the solution was stirred at room temperature for 30 min. The acidic solution was made alkaline with the addition of excess concentrated NH$_4$OH solution. The basic mixture was extracted twice with CH$_2$Cl$_2$. The combined organic solution was washed once with a saturated NaCl solution and dried over MgSO$_4$. The CH$_2$Cl$_2$ solution was evaporated to yield 0.5 g of an oil. Chromatography of this oil over silica gel with ethyl acetate as eluent gave 0.4 g (75%) of product as an oil which upon standing solidified.

mp=76°–77° C.

EXAMPLE 6

Preparation of (+)(2aS,4R)-6-(3-pyrazolyl)-4-(di-n-propylamino)-1,2,2a,3,4,5-hexahydrobenz[cd]indole•2HCL.

A solution of (+)(2aS,4R)-1-triphenylmethyl-6-acetyl-4-(di-n-propylamino)-1,2,2a,3,4,5-hexahydrobenz[cd]indole (1.67 g, 3 mmol) and 3 mL of tris(dimethylamino)methane in 50 mL of toluene was refluxed for 5 hr. The reaction was concentrated in vacuo and the residue was dissolved in 100 mL of CH$_3$OH. To the CH$_3$OH solution was added 2 mL of 85% hydrazine and the reaction mixture was stirred at room temperature for 16 hours. To the reaction mixture was added 50 ml of 1N HCl and stirred for an additional 1 hr. The solution was concentrated in vacuo to remove $CH_3OH$ and the acidic solution was extracted with ethyl acetate. The acidic solution was separated and made alkaline with addition of excess concentrated $NH_4OH$. The basic mixture was extracted with ethyl acetate. The ethyl acetate solution was washed with a brine solution, dried ($MgSO_4$) and concentrated in vacuo to provide 900 mg of an oil. The crude product was chromatographed through silica gel (flash column, ethyl acetate) to yield 700 mg of pyrazole compound. The oil was dissolved in 50 mL of $CH_3OH$ and 2 equivalents of 0.1N HCL was added to the solution. The solution was concentrated in vacuo and the residue was crystallized from ethanol/diethyl ether.

Yield—400 mg mp=260 d MS m/e 324(FD) $[\alpha]_D +19.84°$ (MeOH). Analysis calculated for $C_{20}H_{28}N_4 \cdot 2HCl$ Theory: C, 60.45; H, 7.61; N, 14.10; Found: C, 60.21; H, 7.60; N, 14.26.

EXAMPLE 7

Preparation of (±)-6-(5-isoxazolyl)-4-(di-n-propylamino)-1,2,2a,3,4,5-hexahydrobenz[cd]indole•2HCl.

To a solution of (±)-6-acetyl-4-(di-n-propylamino)-1,2,2a,3,4,5-hexahydrobenz[cd]indole (2.3 g, 7.7 mmol) and triethylamine (1.1 ml, 8 mmol) in 90 ml $CH_2Cl_2$ under $N_2$ was added dropwise a solution of 2,2,2-trichloroethyl chloroformate. The reaction mixture was stirred at room temperature for 1 hr. The $CH_2Cl_2$ solution was extracted with water and 1N HCl. The organic solution was washed with a saturated $NaHCO_3$ solution and with a brine solution. The $CH_2Cl_2$ solution was dried ($MgSO_4$) and concentrated in vacuo to give 3.3 g of the 1-carbamylindoline.

A solution of this 1-carbamylindoline (3.3 g, 7.7 mmol) and tris(dimethylamino)methane (5 mL) in 70 mL of toluene was stirred at reflux for 16 hr. The reaction mixture was concentrated to dryness in vacuo. The residue was dissolved in 50 mL of acetic acid and hydroxylamine hydrochloride (2.5 g, 36 mmol) was added. The reaction mixture was stirred at room temperature for 16 hr and then concentrated in vacuo to dryness. The residue was suspended in water and excess concentrated $NH_4OH$ was added to the mixture. The basic mixture was extracted with $CH_2Cl_2$. The organic solution was washed with a brine solution, dried ($MgSO_4$) and concentrated in vacuo to give 3.1 g of an oil. The crude product was chromatographed (flash column, silica gel, 20% hexanes in ethyl acetate) to yield 2.0 g of (±)-1-carbamyl-6-isoxazolylindoline.

This isoxazole carbamate was dissolved in 20 mL of acetic acid and 1 g of zinc dust was added all at once. The reaction mixture was stirred at room temperature for 4 hr. The reaction mixture was filtered through a celite pad and the filtrate was concentrated to dryness in vacuo. The residue was suspended in a saturated $NaHCO_3$ solution and extracted with $CH_2Cl_2$. The organic solution was washed with a brine solution, dried ($MgSO_4$) and concentrated to an oil. The crude material was chromatographed (flash column, silica gel, ethyl acetate) to give 500 mg of isoxazole indoline. The product was dissolved in 50 mL of $CH_3OH$ and 2 equivalents of 0.1N HCl were added. The solution was concentrated to dryness and the residue was crystallized from ethanol/diethyl ether to give 85 mg of isoxazole substituted product as the dihydrochloride.

mp=226° C. d MS m/e 325(FD) Analysis calculated for $C_{20}H_{27}N_3O \cdot 2HCl$ Theory: C, 60.30; H, 7.34; N, 10.55; Found: C, 58.83; H, 7.18; N, 10.01.

EXAMPLE 8

Preparation of (+)(2aS,4R)-6-(3-isoxazolyl)-4-(di-n-propylamino)-1,2,2a,3,4,5-hexahydrobenz[cd]indole•2 HCl.

A solution of (+)(2aS,4R)-1-triphenylmethyl-6-acetyl-4-(di-n-propylamino)-1,2,2a,3,4,5-hexahydrobenz[cd]indole (3.33 g, 6 mmol), 5 g hydroxylamine hydrochloride, 20 mL pyridine and 30 mL of ethanol was refluxed for 16 hr. The reaction mixture was concentrated to dryness in vacuo and the residue was dissolved in 5N HCl. The acidic mixture was extracted with ethyl acetate. The acidic solution was made alkaline with excess $NH_4OH$ solution and extracted with ethyl acetate. The ethyl acetate solution was washed with a brine solution, dried ($MgSO_4$) and concentrated in vacuo to give 1.5 g of crude product which was chromatographed (flash column, silica gel, ethyl acetate) to give 1.2 g of oxime.

mp=129°–130° C.

To a solution of this oxime (1.2 g, 3.8 mmol) in 100 mL of THF cooled to −5° C. under a $N_2$ atmosphere was added 7.5 mL n-butyllithium (1.6M in hexanes) dropwise with stirring. The reaction mixture was stirred with continued cooling for 1 hr. To the reaction mixture was added 2 mL (26 mmol) of DMF all at once and then stirred for 1 hr at room temperature. The reaction mixture was poured into 50 mL of 1N $H_2SO_4$ and the acidic solution was warmed on a steam bath for 1 hr. The acidic solution was cooled, extracted with diethyl ether, and then made alkaline with excess 5N NaOH. The basic mixture was extracted with ethyl acetate. The organic was layer was washed with a brine solution, dried ($MgSO_4$) and concentrated in vacuo to give 1 g of an oil. The oil was chromatographed (flash column, silica gel, ethyl acetate) to yield 500 mg of product as an oil. The oil was dissolved in 50 mL of $CH_3OH$ and 2 equivalents of 0.1N HCL were added. The solution was concentrated to dryness in vacuo and the residue was crystallized from ethanol/diethyl ether. Crystallization gave 300 mg of the dihydrochloride of the 6-(3-isoxazolyl) product.

mp=215° C. d MS m/e 325(FD) $[\alpha]_D +26.4°$ (MeOH).

EXAMPLE 9

Preparation of (±)-1-benzoyl-6-[4-(2-aminothiazolyl)]-4-(di-n-propylamino)-1,2,2a,3,4,5-hexahydrobenz[cd]indole.

To a solution of (±)-6-acetyl-4-(di-n-propylamino)-1,2,2a,3,4,5-hexahydrobenz[cd]indole (205 mg, 0.7 mmol) and triethylamine (81 mg, 0.8 mmol) in 20 mL of $CH_2Cl_2$ was added a solution of benzoyl chloride (112 mg, 0.8 mmol) in 20 mL of $CH_2Cl_2$. The reaction mixture was stirred at room temperature for 2 hr. The reaction mixture was sucessively washed with water, a saturated $NaHCO_3$ solution, a brine solution and dried ($MgSO_4$). The organic layer was concentrated to dryness in vacuo to give 200 mg of the 1-benzoyl derivative.

A solution of this N-benzoyl compound (200 mg, 0.5 mmol) in 20 mL of acetic acid was saturated with HBr (gas). To the solution was added dropwise a solution of bromine (0.2 mL) in 5 mL of acetic acid. The reaction was stirred at room temperature for 30 min and then concentrated to dryness in vacuo. The residue was dissolved in 30 mL of ethanol then 500 mg of thiourea were added and the mixture refluxed for 16 hr. The reaction was concentrated to dryness in vacuo and the residue dissolved in water. The solution was made alkaline with the addition of concentrated $NH_4OH$. The basic mixture was extracted with $CH_2Cl_2$. The organic solution was washed with a brine solution, dried ($MgSO_4$) and evaporated to dryness to give 200 mg of an oil. The oil was chromatographed (flash column, silica gel, ethyl acetate) to provide 140 mg of the above-named 6-aminothiazolyl compound.

MS m/e 460(FD)

EXAMPLE 10

Preparation of (+) (2aS,4R)-6-(5-isoxazolyl)-4-(di-n-propylamino) -1,2,2a,3,4,5-hexahydrobenz[cd]indole•2 HCl To a solution of (+) (2aS,4R) -6-acetyl-4-(di-n-propylamino)-1,2,2a,3,4,5-hexahydrobenz[cd]indole (1.7 g, 5.7 mmol) and triethylamine (0.8 ml, 6 mmol) in 90 ml $CH_2Cl_2$ was added dropwise a solution of 2,2,2-trichloroethyl chloroformate (1.3 g, 6 mmol) in 10 ml $CH_2Cl_2$. The reaction mixture was stirred at room temperature for one hour and then extracted with water and 1N HCl. The organic solution was washed with a saturated $NaHCO_3$ solution, a saturated brine solution, dried over $MgSO_4$ and then concentrated to dryness in vacuo to give 2.5 g of the 1-carbamylindoline.

A solution of the 1-carbamylindoline (2.5 g, 5.7 mmol) and tris(dimethylamino)methane (5 ml) in 100 ml of toluene was stirred at reflux for 16 hours. After 16 hours the reaction mixture was concentrated to dryness in vacuo. The resulting residue was dissolved in 50 ml of acetic acid and 1.5 g (22 mmol) of a hydroxylamine hydrochloride solution were added. The resulting reaction mixture was stirred at room temperature for 16 hours and then concentrated to dryness in vacuo. The resulting residue was suspended in water and an excess of a concentrated $NH_4OH$ solution was added to the mixture. The basic mixture was then extracted with $CH_2Cl_2$ and the resulting organic extract was washed with a saturated brine solution, dried over $MgSO_4$ and then concentrated in vacuo to give 2.1 g of an oil. This oil was chromatographed (flash column, silica gel, EtOAc) to yield 1.9 g of (+)(2aS,4R)-6-(5-isoxazolyl)indoline. The isoxazolylindoline was dissolved in 30 ml of acetic acid and 1.5 g of zinc dust were added all at once. The resulting reaction mixture was stirred at room temperature for four hours and then filtered through a celite pad. The filtrate thus obtained was then concentrated to dryness in vacuo. The resulting residue was suspended in a saturated $NaHCO_3$ solution, which was then extracted with $CH_2Cl_2$. The organic extract was then washed with a saturated brine solution, dried over $MgSO_4$ and concentrated in vacuo to an oil. This oil was chromatographed (flash column, silica gel, EtOAc) to give 400 mg of isoxazolylindoline. Such compound was dissolved in 50 ml of methanol and two equivalents of 0.1N HCl were added. The resulting solution was concentrated to dryness in vacuo and the resulting residue was then crystallized from ethanol/diethyl ether to give 170 mg of title compound.

mp=235° C. d MS m/e 325(FD) $[\alpha]_D$+27.29° (MeOH) Analysis calculated for $C_{20}H_{27}N_3O$.2HCl Theory: C, 60.30; H, 7.34; N, 10.55; Found: C, 60.53; H, 7.54; N, 10.26.

EXAMPLE 11

Preparation of (−)(2aR,4S)-6-(5-isoxazolyl)-4-(di-n-propylamino)-1,2,2a,3,4,5-hexahydrobenz[cd]indole•2 HCl The title compound was prepared substantially in accordance with the method described in Example 10, above, utilizing 2.5 g (8.3 mmol) of (−)(2aR,4S)-6-acetyl-4-(di-n-propylamino)-1,2,2a,3,4,5-hexahydrobenz[cd]indole (prepared substantially in accordance with the method described in Example 4) and 1.5 g (22 mmol) of a hydroxylamine hydrochloride solution. Such reaction sequence provided 500 mg of title compound.

m.p. 235° C. d MS m/e 325(FD) $[\alpha]_D$31 29.18° (MeOH) Analysis calculated for $C_{20}H_{27}N_3O$.2HCl Theory: C, 60.30; H, 7.34; N, 10.55; Found: C, 60.11; H, 7.41; N, 10.43.

EXAMPLE 12

Preparation of (2aR,4S)-6-(3-phenyl-1,2,4-oxadiazol-5-yl)-4-(di-n-propylamino)-1,2,2a,3,4,5-hexahydrobenz[cd]indole A sodium ethoxide solution was prepared by dissolving 49 mg (2.1 mmol) of sodium in 35 ml of ethanol. Phenylhydroxamidine (1.73 g, 12.71 mmol) and 6-ethoxycarbonyl-4-(di-n-propylamino)-1,2,2a,3,4,5-hexahydrobenz[cd]indole (890 mg, 2.1 mmol) were added to the ethoxide solution and the resulting solution was heated to reflux and stirred at that temperature for 6.25 hours and then stirred overnight at room temperature. The next morning additional sodium ethoxide solution (50 mg of sodium in 10 ml of ethanol) was added and the reaction mixture was again stirred at reflux overnight. The next morning water was added to the reaction mixture and the resulting solution was then extracted with ethyl acetate. The organic extract was washed sequentially with water and a saturated brine solution, dried over sodium sulfate and then concentrated in vacuo to provide 2.33 g of a brown oil. This oil was purified by flash chromatography (2.5% isopropanol in chloroform plus 0.5% ammonium hydroxide) to provide 260 mg of title product as a light yellow solid. Such product was purified by recrystallization from hexane.

Analysis calculated for $C_{25}H_{30}N_4O$ Theory: C, 74.59; H, 7.51; N, 13.92; Found: C, 74.59; H, 7.52; N, 13.90.

EXAMPLE 13

Preparation of (−)(2aR,4S)-6-(2-furyl)-4-(di-n-propylamino)-1,2,2a,3,4,5-hexahydrobenz[cd]indole To a sealable tube with threads containing 13 ml of dry tetrahydrofuran were added 1.2 g (2.46 mmol) of (+)(2aR,4S)-1-benzoyl-6-iodo-4-(di-n-propylamino)-1,2,2a,3,4,5-hexahydrobenz[cd]indole, 968 mg (2.71 mmol) of 2-(tributylstannyl)furan and 200 mg of bis (triphenylphosphine)palladium(II) chloride. The resulting mixture was then deaerated with argon for 15 minutes. After deaeration, the tube was sealed with a teflon cap and the contents thereof were heated to 100° C. for 24 hours. After 24 hours, the reaction mixture was cooled, filtered through a celite pad and the resulting filtrate was then concentrated in vacuo to provide a viscous orange oil. Flash chromatography of this oil over silica gel with 60% ethyl acetate/hexane plus 0.5% ammonium hydroxide as eluent gave the protected analog of the title compound in 61% yield.

The above-mentioned protected analog (635 mg, 1.4 mmol) was dissolved in 10 ml of dry tetrahydrofuran and the resulting solution was chilled to −78° C. Once chilled, 1.5 ml (2.39 mmol) of a 1.7M solution of n-butyllithium in hexane was added dropwise via syringe. Once n-butyllithium addition was complete the reaction mixture was warmed to room temperature. The reaction mixture was quenched with a saturated $NaHCO_3$ solution and then partitioned between ethyl acetate and water. The aqueous layer was extracted with ethyl acetate, and the organic layers were combined, washed with a saturated brine solution, dried over sodium sulfate and then concentrated in vacuo to provide a viscous orange oil. This oil was chromatographed over silica gel (elution with 20% ethyl acetate/hexane plus 0.5% ammonium hydroxide) to provide 161 mg of title compound as a pale yellow oil.

MS m/e 324(FD) $[\alpha]_D$ –45.63° (MeOH) Analysis calculated for $C_{21}H_{28}N_2O$: Theory: C, 77.74; H, 8.70; N, 8.63; Found: C, 78.74; H, 8.82; N, 8.27.

EXAMPLE 14

Preparation of (+)(2aS,4R)-6-(2-furyl)-4-(di-n-propylamino)-1,2,2a,3,4,5-hexahydrobenz[cd]indole The title compound was prepared substantially in accordance with the method set forth in Example 13, above, utilizing 1.5 g (3.07 mmol) of (–)(2aS,4R)-1-benzoyl-6-iodo-4-(di-n-propylamino)-1,2,2a,3,4,5-hexahydrobenz[cd] indole, 250 mg of bis(triphenylphosphine)palladium(II) chloride and 1.21 g (3.38 mmol) of 2-(tributylstannyl)furan to provide 592 mg of title compound as a viscous brown oil.

MS m/e 325.22(FD) $[\alpha]_D$+42.0° (MeOH) Analysis calculated for $C_{21}H_{28}N_2O$: Theory: C, 77.74; H, 8.70; N, 8.63; Found: C, 77.59; H, 8.10; N, 8.83.

EXAMPLE 15

Preparation of (+) (2aS,4R)-6-(3-furyl)-4-(di-n-propylamino)-1,2,2a,3,4,5-hexahydrobenz[cd]indole The title compound was prepared substantially in accordance with the method described in Example 13, above, utilizing 1.50 g (3.07 mmol) of (+)(2aS,4R)-1-benzoyl-6-iodo-4-(di-n-propylamino)-1,2,2a,3,4,5-hexahydrobenz[cd] indole, 1.21 g (3.38 mmol) of 3-(tributylstannyl)furan and 250 mg of bis(triphenylphosphine)palladium(II) chloride to provide 711 mg of title product as a pale yellow viscous oil.

MS m/e 324(FD) Analysis calculated for $C_{21}H_{28}N_2O$: Theory: C, 77.24; H, 8.70; N, 8.63; Found: C, 77.49; H, 8.68; N, 8.45.

EXAMPLE 16

Preparation of (+)(2aS,4R)-6-(2-thienyl)-4-(di-n-propylamino)-1,2,2a,3,4,5-hexahydrobenz[cd]indole The title compound was prepared substantially in accordance with the method set forth in Example 13, above, utilizing 1.5 g (3.1 mmol) of (–)(2aS,4R)-1-benzoyl-6-iodo-4-(di-n-propylamino)-1,2,2a,3,4,5-hexahydrobenz[cd] indole, 150 mg of bis(triphenylphosphine)palladium(II) chloride and 1.27 g (3.41 mmol) of 2-(tributylstannyl) thiophene to provide 719 mg of title compound as a light brown viscous oil.

MS m/e 341(FD) Analysis calculated for $C_{21}H_{28}N_2S$: Theory: C, 74.07; H, 8.29; N, 18.60; S, 9.42; Found: C, 74.24; H, 8.60; N, 17.52; S, 9.15.

EXAMPLE 17

Preparation of (+)(2aS,4R)-6-(2-pyridyl)-4-(di-n-propylamino)-1,2,2a,3,4,5-hexahydrobenz[cd]indole The title compound was prepared substantially in accordance with the method set forth in Example 13, above, utilizing 1.50 g (3.07 mmol) of (–)(2aS,4R)-1-benzoyl-6-iodo-4-(di-n-propylamino)-1,2,2a,3,4,5-hexahydrobenz[cd]indole, 250 mg of bis(triphenylphosphine)palladium(II) chloride and 1.24 g (3.38 mmol) of 2-(tributylstannyl) pyridine to produce 474 mg of title compound as a colorless foam. The hydrochloride salt of the title compound was prepared by dissolving the foam in diethyl ether and then treating the resulting solution with a saturated hydrochloric acid in methanol solution. A yellow foam comprised of such salt was afforded after concentration in vacuo.

MS m/e 336.24(FD) Analysis calculated for $C_{22}H_{29}N_3$·HCl Theory: C, 71.04; H, 8.13; N, 11.30; Found: C, 70.60; H, 8.46; N, 10.58.

EXAMPLE 18

Preparation of (+)(2aS,4R)-6-(3-pyridyl)-4-(di-n-propylamino)-1,2,2a,3,4,5-hexahydrobenz[cd]indole The title compound was prepared substantially in accordance with the procedure set forth in Example 13, above, utilizing 1.50 g (3.07 mmol) of (–)(2aS,4R)-1-benzoyl-6-iodo-4-(di-n-propylamino)-1,2,2a,3,4,5-hexahydrobenz[cd] indole, 250 mg of bis(triphenylphosphine)palladium(II) chloride and 1.24 g (3.38 mmol) of 3-(tributylstannyl) pyridine to produce 475 mg of title compound as a pale yellow oil. The dihydrochloride salt of the title compound was prepared by dissolving the oil in diethyl ether and then adding a saturated hydrochloric acid in methanol solution dropwise. Once an excess of hydrochloric acid had been added the mixture was concentrated in vacuo to provide a pale yellow foam.

MS m/e 336.24(FD) Analysis calculated for $C_{22}H_{29}N_3$·2HCl: Theory: C, 64.70; H, 7.65; N, 10.29; Found: C, 65.84; H, 7.55; N, 9.76.

EXAMPLE 19

Preparation of (–) (2aR,4S)-6-(2-oxazolyl)-4-(di-n-propylamino)-1,2,2a,3,4,5-hexahydrobenz[cd]indole A. 2-tributylstannyloxazole A solution of 1.00 g (14.5 mmol) of oxazole in 25 ml of THF at –78° C. was treated with 10.2 ml (14.6 mmol) of 1.43M butyllithium in hexane. After stirring for 30 minutes, an addition of 3.93 ml (14.5 mmol) of tributyltin chloride was made, and the solution was allowed to warm to room temperature. Stirring was continued for another hour after which most of the solvents were evaporated in vacuo. The resulting residue was taken up in 50 ml of hexane, and the resulting precipitate was separated by filtration through filtercel. Evaporation of the solvent from the filtrate provided 5.13 g of a colorless oil which was identified by NMR as the 2-stannyl derivative plus a small amount of tetrabutylstannane.

B. (2aR,4S)-1-benzoyl-6-(2-oxazolyl)-4-(di-n-propylamino)-1,2,2a,3,4,5-hexahydrobenz[cd]indole A solution of 5.0 g (13.8 mmol) of the crude 2-tributylstannyloxazole prepared above and 6.8 g (13.9 mmol) of (+)(2aR,4S)-1-benzoyl-6-iodo-4-(di-n-propylamino)-1,2,2a,3,4,5-hexahydrobenz[cd]indole in 100 ml of toluene was treated with 0.7 g (0.6 mmol) of tetrakis (triphenylphosphine)palladium then refluxed under nitrogen for 20 hours. After cooling the reaction mixture was washed with a saturated brine solution and then dried over $Na_2SO_4$. Concentration in vacuo provided a viscous oil which was chromatographed over a silica gel column using a solvent gradient progressing from toluene to 1:1 toluene/EtOAc. The product from the column was dissolved in 1M HCl. This solution was then washed with ether, made alkaline with 5M NaOH, and extracted with $CH_2Cl_2$. Concentration of the extract in vacuo gave about 4 g of a brown oil. When this oil was dissolved in pentane a small amount of a red/brown resin separated leaving a clear, yellow solution. The resin was separated and the pentane was evaporated to provide a residue. This residue was crystallized by dissolving it in a small amount of $CH_2Cl_2$ and slowly adding isoctane. The crystalline (−)(2aR,4S)-1-benzoyl-6-(2-oxazolyl)-4-(di-n-propylamino)-1,2,2a,3,4,5-hexahydrobenz[cd]indole, obtained in four crops, weighed 2.63 g. mp 103°–104° C.

C. (−)(2aR,4S)-6-(2-oxazolyl)-4-(di-n-propylamino)-1,2, 2a,3,4,5-hexahydrobenz[cd]indole A solution of 1.00 g (2.33 mmol) of the above 1-benzoyl compound in 25 ml of THF was stirred at −78° C. as 3.0 ml (4.29 mmol) of 1.43M butyllithium in hexane was added. The resulting solution was allowed to warm to 0° C., then poured into water and extracted with $CH_2Cl_2$. The $CH_2Cl_2$ extract was then, in turn, extracted with 1M HCl. The resulting aqueous extract was made alkaline with 1M NaOH, and, in turn, extracted with $CH_2Cl_2$. After drying over $Na_2SO_4$, the extract was concentrated in vacuo to provide title compound as a viscous oil. m.p. 103°–104° C.

MS m/e 326(FD) $[\alpha]_D=-60°$ (MeOH). Analysis calculated for $C_{20}H_{27}N_3O$: Theory: C, 73.81; H, 8.36; N, 12.91; Found: C, 73.37; H, 8.26; N, 12.09.

EXAMPLE 20

Preparation of (−)(2aR,4S)-6-(5-isoxazolyl)-4-[di-(cyclopropylmethyl)amino]-1,2,2a,3,4,5-hexahydrobenz[cd]indole To a solution of (−)(2aR,4S)-6-acetyl-4-[di-(cyclopropylmethyl)amino]-1,2,2a,3,4,5-hexahydrobenz[cd]indole (2.5 g, 7.7 mmol) and triethylamine (1.1 ml, 8 mmol) in 90 ml $CH_2Cl_2$ was added dropwise a solution of 2,2,2-trichloroethylchloroformate (1.7 g, 8 mmol) in 10 ml $CH_2Cl_2$. The reaction mixture was stirred at room temperature for one hour and then extracted with water and 1N HCl. The organic solution was washed with a saturated $NaHCO_3$ solution and a saturated brine solution, dried over $MgSO_4$ and then concentrated to dryness in vacuo to give 3.1 g of the 1-carbamylindoline.

A solution of the 1-carbamylindoline (3.1 g, 6.2 mmol) and tris(dimethylamino)methane (5 ml) in 100 ml of toluene was stirred at reflux for 16 hours. After 16 hours the reaction mixture was concentrated to dryness in vacuo. The resulting residue was dissolved in 50 ml of acetic acid and 2.0 g (29 mmol) of a hydroxylamine hydrochloride solution were added. The resulting reaction mixture was stirred at room temperature for 16 hours and then concentrated to dryness in vacuo. The resulting residue was suspended in water and an excess of a concentrated $NH_4OH$ solution was added to basify the mixture. The basic mixture was then extracted with $CH_2Cl_2$ and the resulting organic extract was washed with a saturated brine solution, dried over $MgSO_4$ and then concentrated in vacuo to give 2.1 g of an oil. This oil was chromatographed (flash column, silica gel, EtOAc) to yield 1.7 g of the protected (+) (2aR,4S)-6-(5-isoxazolyl)indoline.

The above compound (1.7 g, 3.2 mmol) was dissolved in 30 ml of acetic acid and 1.5 g of zinc dust were added all at once. The resulting reaction mixture was stirred at room temperature for four hours and then filtered through a celite pad. The filtrate thus obtained was then concentrated to dryness in vacuo. The resulting residue was suspended in a saturated $NaHCO_3$ solution, then extracted with $CH_2Cl_2$. The organic extract was then washed with a saturated brine solution, dried over $MgSO_4$ and concentrated in vacuo to an oil. This oil was chromatographed (flash column, silica gel, EtOAc) to give 660 mg of title compound.

EXAMPLE 21

Preparation of (−)(2aR,4S)-6-(5-oxazolyl)-4-(di-n-propylamino)-1,2,2a,3,4,5-hexahydrobenz[cd]indole A. (−)(2aR,4S)-6-bromo-1-trityl-4-(di-n-propylamino)-1, 2,2a,3,4,5-hexahydrobenz[cd]indole To a stirred solution of 12.8 g (29 mmol) of (+)(2aR,4S) -1-benzoyl-6-bromo-4-(di-n-propylamino)-1,2,2a,3,4,5-hexahydrobenz[cd]indole in 200 ml of tetrahydrofuran cooled to −78° C. under a nitrogen atmosphere was added 20 ml (32 mmol) of a 1.6M solution of n-butyllithium in hexane. The reaction mixture was stirred at −78° C. for 30 minutes and then allowed to warm to −20° C. To the reaction mixture was added 50 ml of a 1N hydrochloric acid solution. The mixture was extracted once with diethyl ether. The acidic solution was made alkaline with the addition of cold 5N sodium hydroxide solution. The basic mixture was extracted twice with methylene chloride. The combined organic solution was washed with a saturated sodium chloride solution. The methylene chloride solution was dried over magnesium sulfate and evaporated to give 9.6 g of (−)(2aR,4S)-6-bromo-4-(di-n-propylamino)-1,2,2a,3,4,5-hexahydrobenz[cd]indole.

To a solution of the above product (9.6 g, 0.028 mol) and triethylamine (3.03 g, 0.03 mol) in 100 ml of methylene chloride was added a solution of trityl chloride (7.8 g, 0.028 mol) in 100 ml of methylene chloride dropwise at room temperature. The reaction mixture was stirred for 16 hours at room temperature. The reaction mixture was extracted with water and a cold 1N hydrochloric acid solution. The organic solution was washed with a saturated sodium bicarbonate solution and with a saturated brine solution. The organic solution was dried over magnesium sulfate and concentrated to dryness in vacuo to give a residue. The residue was slurried with warm hexane, cooled and filtered to remove insolubles. The filtrate was concentrated to an oil. The oil was chromatographed (silica gel, 20% ethyl acetate in hexane) to provide 12.7 g of the above-titled compound.

B. (−)(2aR,4S)-6formyl-1-trityl-4-(di-n-propylamino)-1, 2,2a,3,4,5-hexahydrobenz[cd]indole To a solution of (−)(2aR,4S)-6-bromo-1-trityl-4-(di-n-propylamino)-1,2,2a,3,4,5-hexahydrobenz[cd]indole (6.8 g, 12 mmol) in 100 ml of tetrahydrofuran cooled to −78° C. under a nitrogen atmosphere was added dropwise a 1.6M solution of n-butyllithium in hexane. The reaction mixture was stirred at −78° C. for 1 hour. Dimethylformamide (3 ml) was added to the reaction mixture and the mixture was stirred at room temperature for 30 minutes. The reaction mixture was quenched with water and then extracted with ethyl acetate. The ethyl acetate solution was washed with a saturated brine solution, dried over magnesium sulfate and concentrated to dryness to provide 5.6 g of the above-titled compound as an oil.

C. (−)(2aR,4S)-6-(5-oxazolyl)-4-(di-n-propylamino)-1,2, 2a,3,4,5-hexahydrobenz[cd]indole A reaction mixture of (−)(2aR,4S)-6-formyl-1-trityl-4-(di-n-propylamino)-1,2,2a,3,4,5-hexahydrobenz[cd]indole (1.06 g, 2 mmol), tosylmethyl isocyanide (390 mg, 2 mmol) and potassium carbonate (304 mg, 2.2 mmol) in 100 ml of methanol was stirred at reflux temperature under a nitrogen atomosphere for 16 hours. The reaction mixture was concentrated to dryness and water was added to the residue. The aqueous mixture was extracted with ethyl acetate. The ethyl acetate solution was washed with a saturated brine solution, dried over magnesium sulfate and concentrated to dryness to yield 1 g of an oil. The oil was dissolved in 20 ml of tetrahydrofuran and 50 ml of 5N hydrochloric acid solution. The reaction mixture was stirred at room temperature for 30 minutes. The reaction mixture was extracted twice with ethyl acetate and the acidic solution was then made alkaline by addition of excess concentrated ammonium hydroxide solution. The basic mixture was extracted twice with ethyl acetate. The ethyl acetate solution was washed with a saturated brine solution, dried over magnesium sulfate and concentrated to dryness to provide 0.5 g of an oil. The oil was purified by silica gel chromatography, with ethyl acetate as eluent, to give 0.3 g of title compound.

MS (FD) m/e/325

EXAMPLE 22

Preparation of (2aR,4S)-6-(3-pyridyl)-4-(di-n-propylamino)-1,2,2a,3,4,5-hexahydrobenz[cd]indole A. 3-pyridylboronic acid A solution of 4.0 ml (6.56 g, 42 mmol) of 3-bromopyridine and 9 ml (8 mmol) of trimethylborate in 100 ml of diethyl ether was cooled to −70° C. then treated slowly with 33 ml (83.8 mmol) of a 2.54M tert-butyllithium in pentane solution. After allowing the resulting slurry to warm to room temperature the solvents were evaporated under vacuum. The residual oil was treated carefully with 50 ml of a 1M hydrochloric acid solution. Several milliters of methylene chloride were added and the mixture was stirred until the oil had dissolved. The aqueous layer was washed with fresh methylene chloride. The pH of the aqueous solution was raised to 12 with 5M sodium hydroxide solution and the washing was repeated. The pH of the aqueous solution was then lowered to 6.5 with concentrated hydrochloric acid solution. After chilling, this solution was filtered, saturated with sodium chloride, then extracted several times with a 2:1 mixture of diethyl ether and isopropanol. Evaporation of these extracts produced a colorless solid. This material was further purified by dissolving in methanol, evaporating to a thick paste, adding a few milliters of water, concentrating further under vacuum, then chilling and collecting the crystalline product. Additional product in the aqueous mother liquor was isolated by repeating this process. Thorough drying of this hydrated product at 0.1 mm pressure afforded a fine powder weighing 2.2 g. Elemental analysis and a mass spectrum indicated the product so isolated was primarily the anhydride (tripyridylboroxane).

B. (2aR,4S)-1-benzoyl-6-(3-pyridyl)-4-(di-n-propylamino)-1,2,2a,3,4,5-hexahydrobenz[cd]indole A solution of 4.00 g of (2aS,4R)-1-benzoyl-6-iodo-4-(di-n-propylamino)-1,2,2a,3,4,5-hexahydrobenz[cd]indole and 0.60 g (0.525 mmol) of tetrakis(triphenylphosphine) palladium in 50 ml of toluene was combined with 10 ml of a 2M sodium bicarbonate solution. This mixture was treated with 1.1 g (9.0 mmol) of the above 3-pyridylboronic anhydride, and it was stirred vigorously at 105° C. under nitrogen for 24 hours. The half-complete reaction was charged with an additional 1.0 g of 3-pyridylboronic anhydride and heating was continued another 24 hours. The cooled mixture was filtered through filtercel. The organic layer was washed with a saturated sodium chloride solution. The toluene was evaporated and the residue was partitioned between 1M hydrochloric acid solution and methylene chloride. The aqueous layer was basified with 5M sodium hydroxide solution and the product was extracted into methylene chloride. After washing with a saturated sodium chloride solution and drying over sodium sulfate the methylene chloride was evaporated leaving a viscous oil. This crude product was chromatographed over a silica gel column using 10% ethyl acetate in toluene, then 25% ethyl acetate in toluene, and finally 1:1 ethyl acetate/toluene as eluent. The purified (2aR,4S) -1-benzoyl-6-(3-pyridyl)-4-(di-n-propylamino)-1,2,2a,3,4,5-hexahydrobenz[cd]indole was an oil weighing 2.99 g.

C. (2aR,4S)-6-(3-pyridyl)-4-(di-n-propylamino)-1,2,2a,3,4,5-hexahydrobenz[cd]indole A solution of 2.75 g (6.26 mmol) of the above 1-benzoyl compound in 50 ml of tetrahydrofuran was stirred at −78° C. as 7.7 ml (11.3 mmol) of a 1.47M butyllithium in hexane solution was added. This solution was allowed to warm to 0° C., then poured into water and extracted with methylene chloride. The methylene chloride was evaporated and the residue was chromatographed over 50 g of florisil using ethyl acetate as eluent. The product from the column was a pale yellow oil weighing 2.0 g which assayed as title product.

EXAMPLE 23

Preparation of (−)(2aR,4S)-6-(3-isoxazolyl)-4-(di-n-propylamino)-1,2,2a,3,4,5-hexahydrobenz[cd]indole To a cool (−5° C.) solution of 2.6 g (3.6 mmol) of (−)(2aR,4S)-1-triphenylmethyl-6-(1-oximidoethane)-4-(di-n-propylamino)-1,2,2a,3,4,5-hexadydrobenz[cd]indole (prepared substantially in accordance with the oxime substrate prepared in Example 8) in 100 ml of tetrahydrofuran was added 6.9 ml of a 1.6M solution of n-butyllithium in hexane. The resulting solution was stirred at −5° C. for one hour and then 2 ml (26 mmol) of dimethylformamide was added all at once. The resulting solution was warmed to room temperature and then stirred for one more hour. After stirring at room temperature for one hour, the reaction solution was poured into 50 ml of a 1N sulfuric acid solution. The acidic solution was warmed on a steam bath for one hour, cooled to room temperature and then extracted with diethyl ether to remove impurities. The acidic solution was made alkaline with excess 5N sodium hydroxide solution and then extracted with ethyl acetate. The extract was washed with a saturated brine solution, dried over magnesium sulfate and then concentrated in vacuo to provide 1 g of an oil. This oil was purified by flash chromatography (using ethyl acetate as eluent) to provide 400 mg of the title compound as an oil.

The present compounds of Formula 1 have been found to have selective affinity for the 5HT receptors in the brain with much less affinity for other receptors. Because of their ability to selectively bind to 5HT receptors, the compounds of Formula 1 are useful in treating disease states which require alteration of 5-HT receptor function, particularly 5-HT$_{1A}$, and/or 5HT$_{1D}$ but without the side effects which may be associated with less selective compounds. This alteration may involve reproducing (an agonist) or inhibiting (an antagonist) the function of serotonin. These disease states include anxiety, depression, excessive gastric acid secretion, motion sickness, hypertension, nausea and vomiting, sexual dysfunction, cognition, senile dementia, migraine, consumptive disorders such as appetite disorders, alcoholism and smoking. The foregoing conditions are treated with a pharmaceutically effective amount of a compound of Formula 1 or a pharmaceutically acceptable salt thereof.

The term "pharmaceutically effective amount", as used herein, represents an amount of a compound of the invention which is capable of diminishing the adverse symptoms of the particular disease. The particular dose of compound administered according to this invention shall, of course, be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical single dose for prophylactic treatment, however, will contain from about 0.01 mg/kg to about 50 mg/kg of the active compound of this invention when administered orally. Preferred oral doses will be about 0.01 to about 3.0 mg/kg, ideally about 0.01 to about 0.1 mg/kg. When a present compound is given orally it may be necessary to administer the compound more than once each day, for example about every eight hours. For IV administration by bolus, the dose will be from about 10 μg/kg to about 300 μg/kg, preferably about 20 μg/kg to about 50 μg/kg.

The following experiments were conducted to demonstrate the ability of the compounds of Formula 1 to bind to 5-HT receptors. Such experiments demonstrate the utility of the compounds of Formula 1 in treating disease states (such as those noted above) which require alteration of 5-HT receptor function.

The affinities of certain of the compounds of Formula 1 at the central 5-$HT_{1A}$ receptors were determined using a modification of the binding assay described by Taylor et al., *J. Pharmacol. Exp. Ther.* 236, 118–125 (1986). Membranes for the binding assay were prepared from male Sprague-Dawley rats (150–250 g). The animals were killed by decapitation, and the brains were rapidly chilled and dissected to obtain the hippocampi. Membranes from the hippocampi were either prepared that day, or the hippocampi were stored frozen (–70° C.) until the day of preparation. The membranes were prepared by homogenizing the tissue in 40 volumes of ice-cold Tris-HCl buffer (50 mM, pH 7.4 at 22° C.) using a Techmar Tissumizer (setting 65 for 15 sec), and the homogenate was centrifuged at 39800xg for 10 minutes. The resulting pellet was then resuspended in the same buffer, and the centrifugation and resuspension process was repeated three additional times to wash the membranes. Between the second and third washes the resuspended membranes were incubated for 10 minutes at 37° C. to facilitate the removal of endogenous ligands. The final pellet was resuspended in 67 mM Tris-HCl, pH 7.4, to a concentration of 2 mg of tissue original wet weight/200 μl. This homogenate was stored frozen (–70° C.) until the day of the binding assay. Each tube for the binding assay had a final volume of 800 μl and contained the following: Tris-HCl (50 mM), pargyline, (10 μM), $CaCl_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes were incubated for 10 minutes at 37° C. and the contents were then rapidly filtered through GF/B filters (pretreated with 0.5% polyethylenimine), followed by four 1 ml washes with ice-cold buffer. The radioactivity trapped by the filters was quantitated by liquid scintillation spectrometry, and specific [$^3$H]8-OH-DPAT binding to the 5-$HT_{1A}$ sites was defined as the difference between [$^3$H]8-OH-DPAT bound in the presence and absence of 10 μM 5-HT.

The results of the evaluation of various compounds of Formula 1 in the test system described above are set forth in Table 1, below. In Table 1, the first column provides the Example Number of the compound evaluated while the second column provides the amount of test compound (expressed in nanomolar concentration) required to inhibit the binding of [$^3$H]8-OH-DPAT by 50% (indicated as $IC_{50}$).

TABLE 1

| IN VITRO BINDING ACTIVITY AT THE 5-HT1A RECEPTOR | |
|---|---|
| Example No. | 5-HT1A in vitro binding ($IC_{50}$, nM) |
| 6 | 6.37 |
| 7 | 1.95 |
| 8 | 0.91 |
| 10 | 0.73 |
| 11 | 2.08 |
| 12 | 105.00 |
| 13 | 21.09 |
| 14 | 5.30 |
| 15 | 2.74 |
| 17 | 17.34 |
| 18 | 1.92 |

The affinities of certain of the compounds of Formula 1 at the central 5-$HT_{1D}$ binding sites were determined using a modification of the binding assay described by Heuring and Peroutka, *J. Neurosci.*, 7, 894 (1987). Bovine brains were obtained and the caudate nuclei were dissected out and frozen at –70° C. until the time that the membranes were prepared for the binding assays. At that time the tissues were homogenized in 40 volumes of ice-cold Tris-HCl buffer (50 mM, pH 7.4 at 22° C.) with a Techmar Tissumizer (setting 65 for 15 sec), and the homogenate was centrifuged at 39,800xg for 10 minutes. The resulting pellet was then resuspended in the same buffer, and the centrifugation and resuspension process was repeated three additional times to wash the membranes. Between the second and third washes the resuspended membranes were incubated for 10 minutes at 37° C. to facilitate the removal of endogenous 5-HT. The final pellet was resuspended in the buffer to a concentration of 25 mg of original tissue wet weight/ml for use in the binding assay. Each tube for the binding assay had a final volume of 800 μl and contained the following: Tris-HCl (50 mM), pargyline (10 μM), ascorbate (5.7 mM), $CaCl_2$ (3 mM), 8-OH-DPAT (100 nM to mask 5-$HT_{1A}$ receptors), mesulergine (100 nM to mask 5-$HT_{1C}$ receptors), [$^3$H]5-HT (1.7–1.9 nM), appropriate dilutions of the drugs of interest, and membrane resuspension equivalent to 5 mg of original tissue wet weight, for a final pH of 7.4. The assay tubes were incubated for 10 minutes at 37° C. and the contents were then rapidly filtered through GF/B filters (pretreated with 0.5% polyethylenimine), followed by four 1 ml washes with ice-cold buffer. The radioactivity trapped by the filters was quantitated by liquid scintillation spectrometry, and specific [$^3$H]5-HT binding to the 5-$HT_{1D}$ sites was defined as the difference between [$^3$H]5-HT bound in the presence and absence of 10 μM 5-HT.

The results of the evaluation of various compounds of Formula 1 in the test system described above are set forth in Table 2, below. In Table 2, the first column provides the Example Number of the compound evaluated while the second column provides the amount of test compound (expressed in nanomolar concentration) required to inhibit the binding of [$^3$H]5-HT by 50% (indicated as $IC_{50}$).

TABLE 2

IN VITRO BINDING ACTIVITY AT THE 5-HT1D RECEPTOR

| Example No. | 5-HT1D in vitro binding ($IC_{50}$, nM) |
| --- | --- |
| 6 | 30.00 |
| 7 | 23.58 |
| 8 | 9.12 |
| 10 | 11.24 |
| 11 | 1375.00 |
| 13 | 1887.62 |
| 14 | 43.14 |
| 15 | 19.40 |
| 17 | 163.02 |
| 18 | 40.29 |

The compounds of the present invention are preferably formulated prior to administration. Therefore, yet another embodiment of the present invention is a pharmaceutical formulation comprising a compound of the invention and a pharmaceutically acceptable excipient therefor. The present pharmaceutical formulations are prepared by known procedures using well known and readily available ingredients. In making the compositions of the present invention, the active ingredient will usually be mixed with an excipient, diluted by an excipient or enclosed within an excipient serving as a carrier which can be in the form of a capsule, sachet, paper or other container. When the excipient serves as a diluent, it can be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl and propylhydroxybenzoates, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 0.5 to about 50 mg, more usually about 1 to about 10 mg of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The following formulation examples are illustrative only and are not intended to limit the scope of the invention in any way.

Formulation 1

Hard gelatin capsules are prepared using the following ingredients:

| | Quantity (mg/capsule) |
| --- | --- |
| (+)-6-(3-isoxazolyl)-4-(di-n-propylamino)-1,2,2a,3,4,5-hexahydrobenz[cd]indole | 25 |
| Starch, dried | 425 |
| Magnesium stearate | 10 |
| Total | 460 mg |

The above ingredients are mixed and filled into hard gelatin capsules in 460 mg quantities.

Formulation 2

A tablet formula is prepared using the ingredients below:

| | Quantity (mg/tablet) |
| --- | --- |
| (±)-6-[3-(5-aminothiazolyl)]-4-(di-n-propylamino)-1,2,2a,3,4,5-hexahydrobenz[cd]indole | 25 |
| Cellulose, microcrystalline | 625 |
| Colloidal silicon dioxide | 10 |
| Stearic acid | 5 |

The components are blended and compressed to form tablets each weighing 665 mg.

Formulation 3

A dry powder inhaler formulation is prepared containing the following components:

| | Weight % |
| --- | --- |
| (±)-6-(5-isoxazolyl)-4-(di-n-propylamino)-1,2,2a,3,4,5-hexahydrobenz[cd]indole | 5 |
| Lactose | 95 |

The active compound is mixed with the lactose and the mixture added to a dry powder inhaling appliance.

Formulation 4

Tablets each containing 60 mg of active ingredient are made up as follows:

| | |
| --- | --- |
| (+)-6-(2-pyrazolyl)-4-(di-n-propylamino)-1,2,2a,3,4,5-hexahydrobenz[cd]indole | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°–60° C. and passed through a No. 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 150 mg.

Formulation 5

Capsules each containing 20 mg of medicament are made as follows:

| | |
|---|---|
| (±)-6-(5-oxadiazolyl)-4-(dimethylamino)-1,2,2a,3,4,5-hexahydrobenz[cd]indole | 20 mg |
| Starch | 169 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

Formulation 6

Suppositories each containing 225 mg of active ingredient are made as follows:

| | |
|---|---|
| (+)-6-(4-pyridyl)-4-(di-n-propylamino)-1,2,2a,3,4,5-hexahydrobenz[cd]indole | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| (±)-6-(2-thiazolyl)-4-(di-n-propylamino)-1,2,2a,3,4,5-hexahydrobenz[cd]indole | 50 mg |
| Xanthan gum | 4 mg |
| Sodium carboxymethyl cellulose (11%) Microcrystalline cellulose (89%) | 50 mg |
| Sucrose | 1.75 g |
| Sodium benzoate | 10 mg |
| Flavor | q.v. |
| Color | q.v. |
| Purified water to | 5 ml |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and color are diluted with some of the water and added with stirring. Sufficient water is then added to produce the required volume.

Formulation 8

Capsules each containing 50 mg of medicament are made as follows:

| | |
|---|---|
| (+)-6-(5-isoxazolyl)-4-(dimethylamino)-1,2,2a,3,4,5-hexahydrobenz-[cd]indole | 50 mg |
| Starch | 507 mg |
| Magnesium stearate | 3 mg |
| Total | 560 mg |

The active ingredient, cellulose, starch and magnesium stearate are blended, passed through a No. 20 mesh U.S. sieve, and filled into hard gelatin capsules.

We claim:

1. A compound of the formula

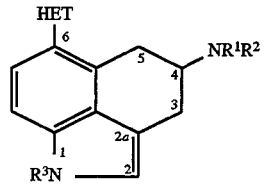

wherein:

$R^1$ is hydrogen, $C_1$–$C_4$ alkyl, $C_3$–$C_4$ alkenyl, cyclopropylmethyl, phenyl ($C_1$–$C_4$ alkyl), naphthyl ($C_1$–$C_4$ alkyl), phenyl ($C_1$–$C_4$ alkyl) substituted with one or two substituents selected from the group consisting of $C_1$–$C_3$ alkoxy, halo, hydroxy, $C_1$–$C_3$ thioalkyl, nitro, $C_1$–$C_3$ alkyl or trifluoromethyl, naphthyl ($C_1$–$C_4$ alkyl) substituted with one or two substituents selected from the group consisting of $C_1$–$C_3$ alkoxy, halo, hydroxy, $C_1$–$C_3$ thioalkyl, nitro, $C_1$–$C_3$ alkyl or trifluoromethyl, —$(CH_2)_nS(C_1$–$C_4$ alkyl), —$C(O)R^4$, —$(CH_2)_nC(O)NR^5R^6$;

$R^2$ is hydrogen, $C_1$–$C_4$ alkyl, cyclopropylmethyl or $C_3$–$C_4$ alkenyl;

$R^3$ is hydrogen, $C_1$–$C_4$ alkyl or an amino blocking group;

n is 1–4;

$R^4$ is hydrogen, $C_1$–$C_4$ alkyl, $C_1$–$C_4$ haloalkyl, $C_1$–$C_4$ alkoxy or phenyl;

$R^5$ and $R^6$ are independently hydrogen, $C_1$–$C_4$ alkyl, or $C_5$–$C_8$ cycloalkyl with the proviso that when one of $R^5$ or $R^6$ is a cycloalkyl the other is hydrogen;

HET is a heterocyclic ring selected from the group consisting of

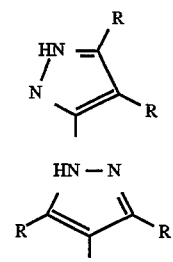

where R is hydrogen, $C_1$–$C_3$ alkyl, halogen, hydroxy, $C_1$–$C_3$ alkoxy, $C_1$–$C_3$ thioalkyl, $NH_2$, CN or phenyl; or pharmaceutically acceptable salts thereof.

2. The compounds of claim 1 wherein $R^1$ and $R^2$ are independently $C_1$–$C_3$ alkyl or a pharmaceutically acceptable salt thereof.

3. The compounds of claim 1 wherein $R^3$ is hydrogen or a pharmaceutically acceptable salt thereof.

4. The compounds of claim 3 wherein $R^3$ is hydrogen or a pharmaceutically acceptable salt thereof.

5. The compounds of claim 1 wherein $R^1$ is —$(CH_2)_nC(O)NR^5R^6$ wherein n is 2, $R^5$ is hydrogen, $R^6$ is cyclohexyl, $R^2$ is $C_1$–$C_3$ alkyl, and $R^3$ is hydrogen or $C_1$–$C_4$ alkyl or a pharmaceutically acceptable salt thereof.

6. The substantially pure stereoisomer of a compound of claim 1 or a pharmaceutically acceptable salt thereof.

7. The stereoisomer of claim 6 wherein the configuration at position 2a is R and at position 4 is S or a pharmaceutically acceptable salt thereof.

8. A compound of claim 1 selected from the group consisting of 6-(3-pyrazolyl)-4-(di-n-propylamino)-1,2,2a,3,4,5-hexahydrobenz[cd]indole; 6-(4-pyrazolyl)-4-(dimethylamino)-1,2,2a,3,4,5-hexahydrobenz[cd]indole; +(2aS,4R)-6-(3-pyrazolyl)-4-(di-n-propylamino)-1,2,2a,3,4,5-hexahydrobenz[cd]indole, or a pharmaceutically acceptable salt thereof.

9. The substantially pure stereoisomer of a compound of claim 8 wherein the configuration at position 2a is S and at position 4 is R or a pharmaceutically acceptable salt thereof.

10. A pharmaceutical formulation comprising a therapeutically effective amount of a compound of claim 1 or a pharmaceutically acceptable salt thereof in combination with a pharmaceutically acceptable excipient therefor.

11. A method for treating a mammal with a serotonin-related disorder selected from the group consisting of anxiety, depression, excessive gastric acid secretion, hypertension, nausea and vomiting, motion sickness, senile dementia, appetite disorders, alcoholism and smoking which comprises administering to said mammal an effective amount of a compound of claim 1 or a pharmaceutically acceptable salt thereof.

* * * * *